United States Patent
Tsuruta et al.

(10) Patent No.: US 10,264,956 B2
(45) Date of Patent: Apr. 23, 2019

(54) ENDOSCOPE SYSTEM HAVING PROCESSOR FOR CALCULATING A SIZE OF A CONVEX PORTION

(71) Applicant: OLYMPUS CORPORATION, Tokyo (JP)

(72) Inventors: Misa Tsuruta, Hachioji (JP); Satoshi Takekoshi, Hachioji (JP); Yuichi Takeuchi, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 121 days.

(21) Appl. No.: 15/392,312

(22) Filed: Dec. 28, 2016

(65) Prior Publication Data

US 2017/0105613 A1  Apr. 20, 2017

Related U.S. Application Data

(63) Continuation of application No. PCT/JP2015/063305, filed on May 8, 2015.

(30) Foreign Application Priority Data

Sep. 25, 2014  (JP) .................... 2014-195589

(51) Int. Cl.
*A61B 1/00* (2006.01)
*A61B 1/06* (2006.01)
(Continued)

(52) U.S. Cl.
CPC ........ *A61B 1/0615* (2013.01); *A61B 1/00009* (2013.01); *A61B 1/00089* (2013.01);
(Continued)

(58) Field of Classification Search
CPC .... A61B 1/00; A61B 1/04; A61B 1/05; A61B 1/051; A61B 1/06; A61B 5/1075;
(Continued)

(56) References Cited

U.S. PATENT DOCUMENTS 6,563,105 B2 * 5/2003 Seibel .................. A61B 1/0008
250/208.1
2010/0079757 A1 4/2010 Murooka et al.

FOREIGN PATENT DOCUMENTS

EP 0075415 A2 3/1983
JP S58-44030 A 3/1983
(Continued)

OTHER PUBLICATIONS

International Search Report dated Aug. 4, 2015 issued in PCT/JP2015/063305.

(Continued)

*Primary Examiner* — John P Leubecker
*Assistant Examiner* — William Chou
(74) *Attorney, Agent, or Firm* — Scully, Scott, Murphy & Presser, P.C.

(57) ABSTRACT

An endoscope system includes a convex-portion specifying section that detects a convex portion in a picked-up image of a subject picked up by an image pickup section, and a convex-portion-size calculating section that detects a convex portion in a predetermined size range on the basis of information concerning the convex portion. An illumination section includes a plurality of illumination-light emitting sections that illuminate the subject with lights in bands different from one another from directions different from one another. The plurality of illumination-light emitting sections are provided on a distal end side inner circumferential surface of a cylindrical cap attached to the distal end of an insertion section of an endoscope to specify an image pickup range of the image pickup section.

4 Claims, 18 Drawing Sheets

(51) Int. Cl.
    *A61B 1/04*      (2006.01)
    *G02B 23/24*     (2006.01)
    *A61B 1/012*     (2006.01)
    *A61B 1/05*      (2006.01)
    *A61B 5/00*      (2006.01)
    *A61B 5/107*     (2006.01)

(52) U.S. Cl.
    CPC ........ *A61B 1/00096* (2013.01); *A61B 1/0125* (2013.01); *A61B 1/05* (2013.01); *A61B 1/0623* (2013.01); *A61B 1/0638* (2013.01); *A61B 1/0676* (2013.01); *A61B 5/0084* (2013.01); *A61B 5/1076* (2013.01); *G02B 23/24* (2013.01); *A61B 1/00133* (2013.01)

(58) Field of Classification Search
    CPC ....... A61B 5/1076; A61B 5/065; A61B 90/06; A61B 2090/061; G06T 2207/10068
    USPC ....... 600/109, 117, 118, 138, 139, 160, 166, 600/167, 176, 178
    See application file for complete search history.

(56) References Cited

FOREIGN PATENT DOCUMENTS

| | | |
|---|---|---|
| JP | 2003-164419 A | 6/2003 |
| JP | 2009-273655 A | 11/2009 |
| JP | 2010-082271 A | 4/2010 |
| JP | 2011-183000 A | 9/2011 |

OTHER PUBLICATIONS

Japanese Office Action dated May 24, 2016 issued in Japanese Patent Application No. 2016-501262.

* cited by examiner

ENDOSCOPE SYSTEM HAVING PROCESSOR FOR CALCULATING A SIZE OF A CONVEX PORTION

CROSS REFERENCE TO RELATED APPLICATION

This application is a continuation application of PCT/JP2015/063305 filed on May 8, 2015 and claims benefit of Japanese Application No. 2014-195589 filed in Japan on Sep. 25, 2014, the entire contents of which are incorporated herein by this reference.

BACKGROUND OF THE INVENTION

1. Field of the Invention

The present invention relates to an endoscope system capable of detecting a convex portion in a body cavity.

2. Description of the Related Art

There has been widely used a medical endoscope that inserts an elongated insertion section into a curved body cavity to thereby observe organs and the like in deep parts in the body cavity without dissecting a body surface and realizes various kinds of therapy, treatment, and the like using a treatment instrument inserted through a treatment instrument channel of an endoscope insertion section according to necessity.

There has been also performed laparoscopy for enabling, using a laparoscope as an endoscope, therapy and treatment while observing a treatment instrument and a treatment region without performing abdominal operation. The laparoscopy has an advantage that invasion into a patient is alleviated. However, in the laparoscopy, it is hard to check a very small convex lesion part in a body cavity.

For example, a peritoneum lesion of endometriosis has a very small and transparent blister-like convex shape. A generation region of the peritoneum lesion extends to a side range such as an abdominal wall, organs in an abdominal cavity, a surface layer of a human body, and the like. Therefore, the peritoneum lesion is easily overlooked in the laparoscopy.

As an apparatus that detects such a lesion part, Japanese Patent Application Laid-Open Publication No. 2010-82271 (hereinafter referred to as Literature 1) proposes an apparatus that detects very small unevenness in a body cavity. Japanese Patent Application Laid-Open Publication No. 2009-273655 (hereinafter referred to as Literature 2) proposes an image processing system that specifies a shape of an object surface.

Incidentally, in such an apparatus that detects a convex portion, which is a lesion part, a size of a convex portion of a lesion part desired to be detected is often limited to a predetermined size range. For example, a convex portion having a size too small as a lesion part does not need to be detected. A convex portion having a size that can be surely checked by the laparoscopy or the like does not particularly need to be detected either. For example, a convex portion having a size larger than a predetermined maximum size (e.g., 5 mm) and a convex portion having a size smaller than a predetermined minimum size (e.g., 1 mm) sometimes do not need to be detected.

SUMMARY OF THE INVENTION

An endoscope system according to an aspect of the present invention includes: an illumination section that radiates illumination light and illuminates a predetermined illumination range; an image pickup section that picks up an image of a predetermined image pickup range of a subject illuminated by the illumination section; a convex-portion specifying section that detects a convex portion in the picked-up image of the subject picked up by the image pickup section; and a convex-portion-size calculating section that detects a convex portion in a predetermined size range on the basis of information concerning the convex portion detected by the convex-portion specifying section. The illumination section includes a plurality of illumination-light emitting sections that illuminate the subject with lights in bands different from one another from directions different from one another. The image pickup section is attached to a distal end of an insertion section of an endo scope and includes an optical axis in an axial direction of the insertion section. The plurality of illumination-light emitting sections are provided on a distal end side inner circumferential surface of a cylindrical cap attached to the distal end of the insertion section to specify an image pickup range of the image pickup section.

DETAILED DESCRIPTION OF THE PREFERRED EMBODIMENT(S)

Embodiments of the present invention are explained in detail below with reference to the drawings.

First Embodiment

Figure 1:
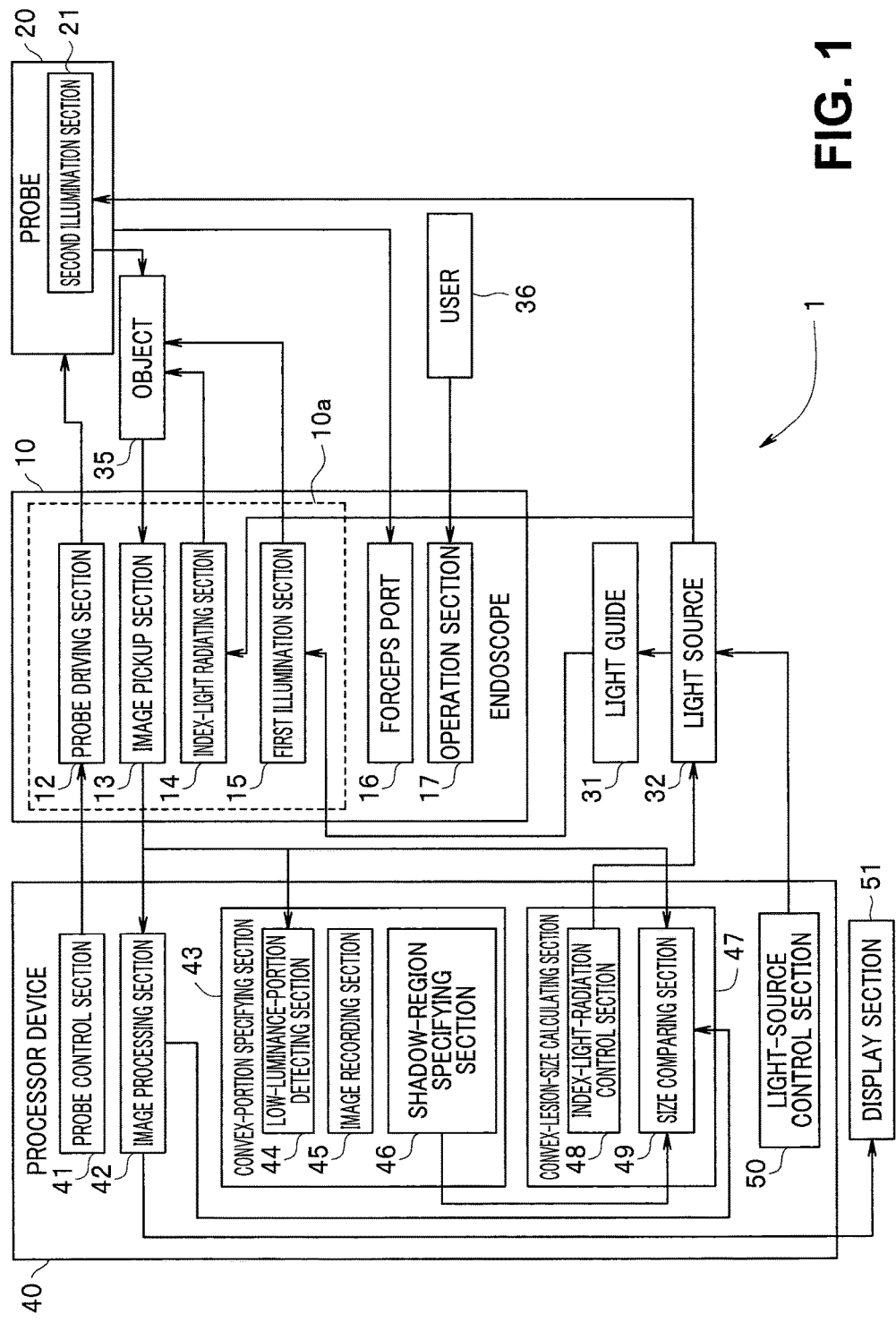
FIG. 1 is a block diagram showing an endoscope system according to a first embodiment of the present invention.
Figure 2:
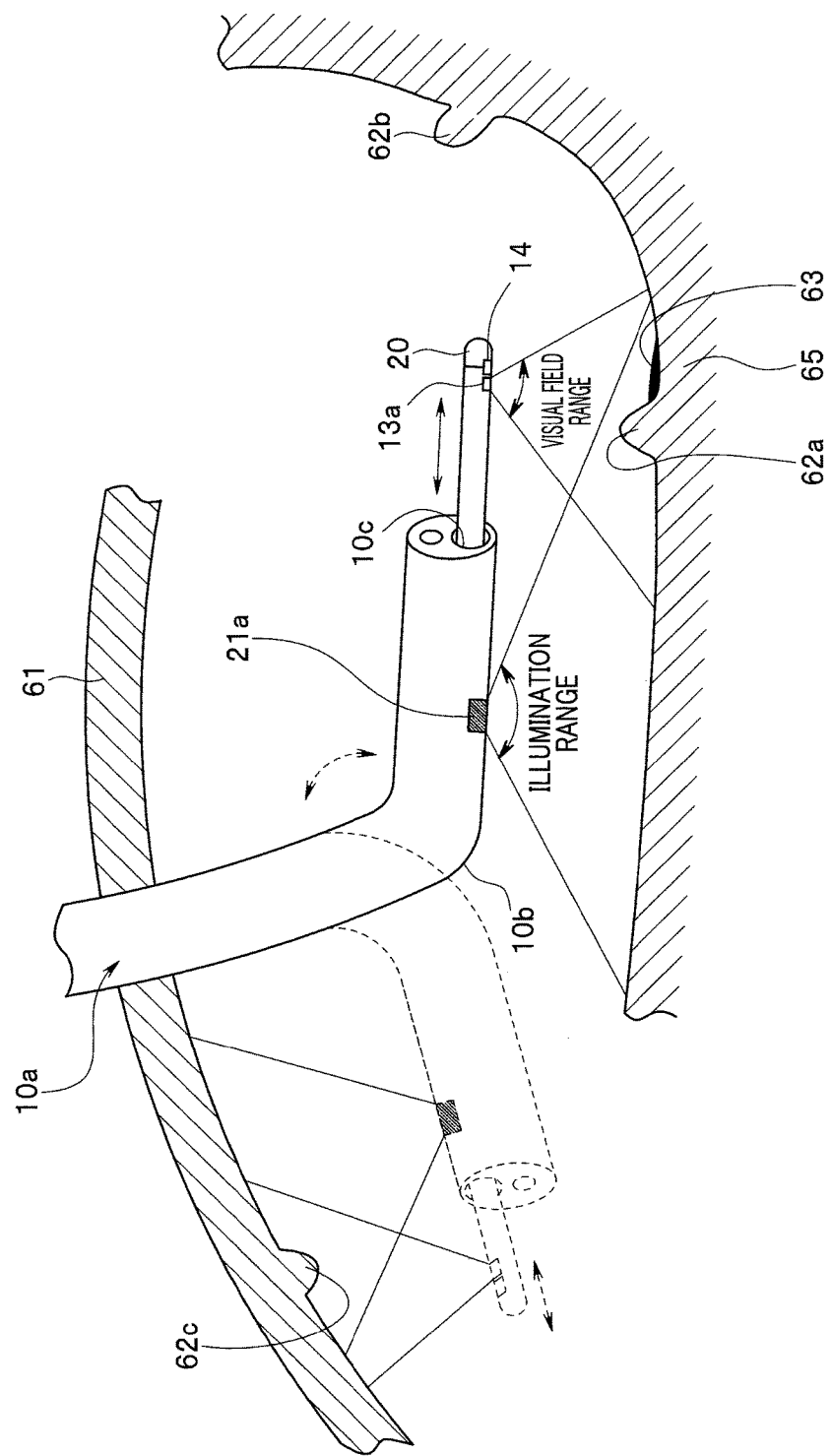
FIG. 2 is an explanatory diagram showing a state in which an insertion section of the endoscope is inserted into a body cavity.

FIG. 1 is a block diagram showing an endoscope system according to a first embodiment of the present invention. FIG. 2 is an explanatory diagram showing a state in which an insertion section of an endoscope is inserted into a body cavity.

An endoscope system 1 includes an endoscope 10, a probe 20, and a processor device 40. The endoscope 10 includes an elongated insertion section 10a having flexibility inserted into a body cavity. FIG. 2 shows a state in which the insertion section 10a is inserted into the body cavity via an abdominal wall 61 of a patient, who is a subject.

Note that the insertion section 10a in FIG. 2 includes a configuration different from a configuration shown in FIG. 1. The following explanation concerns FIG. 1 unless specifically noted otherwise.

In FIG. 1, an operation section 17, on which various operation devices are provided, is provided on a proximal end side of the insertion section 10a. A cable is extended from the operation section 17. The endoscope 10 and the processor device 40 are detachably connected via the cable. Note that, although not illustrated for simplification of the drawing in FIG. 1, electrical connection between respective sections in the insertion section 10a and the processor device 40 is performed via the operation section 17.

A forceps port 16 is provided in the endoscope 10. In the insertion section 10a, a not-shown channel piercing through from the forceps port 16 to a distal end opening 10c (see FIG. 2) of the insertion section 10a is provided. The probe 20 is disposed in the channel to be capable of advancing and retracting.

The operation section 17 can receive operation of a user 36 on the various operation devices and control operation of driving of the respective sections. For example, a bending section 10b (see FIG. 2) is provided in the insertion section 10a. The bending section 10b is configured to actively bend in up-down and left-right directions according to operation by the user 36 on a not-shown bending operation knob provided in the operation section 17.

In the present embodiment, a probe driving section 12 is provided in the insertion section 10a. The probe driving section 12 is configured by a not-shown motor or the like and can advance and retract the probe 20 in the channel and can change a projection amount of the probe 20 from the distal end opening 10c.

The endoscope system 1 includes a light source 32. The light source 32 generates illumination light and supplies, via a light guide 31, the illumination light to a first illumination section 15 disposed in the insertion section 10a. The first illumination section 15 is configured by, for example, a lens (not shown in the figure) disposed at a distal end of the insertion section 10a and can radiate the illumination light on an object 35.

The light source 32 also supplies the generated illumination light to a second illumination section 21 disposed, for example, on a side surface of the probe 20. The second illumination section 21 includes an optical axis, for example, in a substantially perpendicular direction with respect to an advancing and retracting direction of the probe 20 and can radiate the illumination light on the object 35.

Note that, in FIG. 1, an example is shown in which illumination light is supplied to the first illumination section 15 via the light guide 31. However, a setting position of the light source 32 and a transmission route of the illumination light are not particularly limited. The first and second illumination sections 15 and 21 may include light sources. Illumination may be supplied to the second illumination section 21 via a light guide. For example, at least one of the first illumination section 15 and the second illumination section 21 may be configured by an LED or the like. In this case, the light source 32 supplies electric power to the first illumination section 15 or the second illumination section 21 configured by the LED to control lighting.

An image pickup section 13 is also provided in the insertion section 10a of the endoscope 10. The image pickup section 13 is disposed, for example, on a side surface of the insertion section 10a such that a visual field range of the image pickup section 13 overlaps an illumination range of the first and second illumination sections 15 and 21. Object reflected light (return light) of the illumination light from the first and second illumination sections 15 and 21 radiated on the object 35 is made incident on an image pickup surface of the image pickup section 13. The image pickup section 13 converts an object optical image made incident on the image pickup surface into an electric signal and outputs a picked-up image.

As explained above, the probe 20 is driven by the probe driving section 12 to advance and retract. A projection amount from the distal end opening 10c changes. That is, relative positions of the image pickup section 13 and the second illumination section 21 change according to advancing and retracting movements of the probe 20.

In the present embodiment, image pickup is performed while relatively changing an illumination direction of illumination light with respect to the object 35 and a visual field direction in the image pickup. Therefore, when the image pickup section 13 is provided in the insertion section 10a as shown in FIG. 1, the illumination is performed by the second illumination section 21 provided in the probe 20 and the image pickup by the image pickup section 13 is performed while advancing and retracting the probe 20. Consequently, it is possible to relatively change a position of the second illumination section 21 and a position of the image pickup section 13. It is possible to perform the image pickup while relatively changing the illumination direction and the visual field direction.

Note that a configuration is also conceivable in which an image pickup section is provided on the probe 20 side. In this case, a second illumination section is provided on the insertion section 10a side to illuminate the object 35. In this case as well, by advancing and retracting the probe 20, it is possible to change a relative positional relation between the image pickup section provided in the probe 20 and the second illumination section that illuminates the object 35. Note that FIG. 2 shows an example of this case. An image pickup section 13a is provided in the probe 20 and a second illumination section 21a is provided in the insertion section 10a.

Note that, in the present embodiment, in the following explanation, an example is explained in which a convex portion is detected using the image pickup section 13 provided in the insertion section 10a and the second illumination section 21 provided in the probe 20. A method of detecting a convex portion using the second illumination section 21a provided in the insertion section 10a and the image pickup section 13a provided in the probe 20 can be considered the same. Therefore, explanation of the method is omitted.

In the present embodiment, an index-light radiating section 14 is provided in the endoscope 10. The index-light radiating section 14 can radiate parallel light, a size of light beams of which is a specified value. Note that the index-light radiating section 14 only has to be provided in a position where the index-light radiating section 14 is capable of irradiating the object 35. In FIG. 1, an example is shown in which the index-light radiating section 14 is provided in the insertion section 10a. In FIG. 2, an example is shown in which the index-light radiating section 14 is provided in the probe 20.

The processor device 40 includes a not-shown processor such as a CPU. Respective sections in the processor device 40 can be controlled by the processor. A light-source control section 50 is provided in the processor device 40. The light-source control section 50 can control the light source 32 and cause the first or second illumination section 15 or 21 to radiate illumination light on the object 35.

The processor device 40 includes a not-shown driving circuit that drives the image pickup section 13 of the endoscope 10 and includes an image processing section 42 to which a picked-up image from the image pickup section 13 is inputted. The image processing section 42 applies predetermined image signal processing to the inputted picked-up image and outputs the picked-up image to a display section 51. The display section 51 displays the picked-up image given from the image processing section 42.

In the present embodiment, a probe control section 41 is provided in the processor device 40. The probe control section 41 can control driving of the probe driving section 12 provided in the endoscope 10 and advance and retract the probe 20 by a set distance.

In the present embodiment, a convex portion having a predetermined size is determined as a convex lesion part. For the determination, as shown in FIG. 2, a surgeon inserts the insertion section 10a into the body cavity via the abdominal wall 61 and disposes the insertion section 10a near a region desired to be observed. In the example shown in FIG. 2, an example is shown in which a convex portion 62a among a plurality of convex portions 61a to 62c present in the body cavity is detected. In this case, a state is shown in which a distal end side of the insertion section 10a and an axial direction of the probe 20 are disposed in substantially parallel to an observation region 65, and a convex portion 62a in the observation region 65 is in an illumination range of the second illumination section 21a (in FIG. 1, the second illumination section 21) and in a visual field range of the image pickup section 13a (in FIG. 1, the image pickup section 13). In this state, in the present embodiment, presence of the convex portion 62a in the observation region 65 is detected, a size of the detected convex portion 62a is calculated, and, when the convex portion 62a is in a predetermined size range, it is determined that the convex portion 62a is a convex lesion part.

In order to detect the presence of the convex portion 62a in the observation region 65, a convex-portion specifying section 43 is provided in the processor device 40. The convex-portion specifying section 43 is configured by a low-luminance-portion detecting section 44, an image recording section 45, and a shadow-region specifying section 46. Picked-up images corresponding to illumination of the illumination section 21 before and after the change in the relative positions of the image pickup section 13 and the illumination section 21 are given to the low-luminance-portion detecting section 44 from the image pickup section 13. The low-luminance-portion detecting section 44 detects low luminance portions in the respective picked-up images.

For example, the low-luminance-portion detecting section 44 may calculate, as the low luminance portions, pixels having luminance lower than a predetermined threshold in the picked-up images. The low-luminance-portion detecting section 44 gives a detection result concerning positions, shapes, and sizes of the low luminance portions detected concerning the respective picked-up images to the image recording section 45. The detection result of the low-luminance-portion detecting section 44 is recorded in the image recording section 45. For example, the low-luminance-portion detecting section 44 may calculate the sizes of the low luminance portions according to the numbers of pixels of the detected low luminance portions.

The probe control section 41 advances and retracts the probe 20 before and after the detection by the low-luminance-portion detecting section 44. Consequently, the low-luminance-portion detecting section 44 detects the low luminance portions before and after the advance and retraction of the probe 20, that is, before and after the change in the relative positions of the image pickup section 13 and the illumination section 21. In the image recording section 45, a detection result of the low luminance portions before and after the advance and retraction of the probe 20 is recorded.

The shadow-region specifying section 46 reads out the detection result of the low-luminance-portion detecting section 44 from the image recording section 45. When it is indicated by the detection result of the low luminance portions that the shapes of the low luminance portions change before and after the change in the relative positions of the image pickup section 13 and the illumination section 21, the shadow-region specifying section 46 determines that the low luminance portions as convex portions and outputs a determination result of the sizes of the low luminance portions to a size comparing section 49 of a convex-lesion-size calculating section 47.

The convex-lesion-size calculating section 47 is configured by an index-light-radiation control section 48 and the size comparing section 49. The index-light-radiation control section 48 controls the light source 32 to radiate illumination light from the index-light radiating section 14 on the object 35.

A picked-up image based on illumination of the index-light radiating section 14 is given to the size comparing section 49 from the image pickup section 13. The size comparing section 49 calculates a size of index light in the inputted picked-up image and performs comparison with the sizes of the low luminance portions given from the image recording section 45 to calculate sizes of the convex portions. When the calculated sizes of the convex portions are sizes within a specified range, the size comparing section 49 determines that the convex portions are lesion parts and outputs information concerning the convex portions (not shown in the figure).

Figure 3:
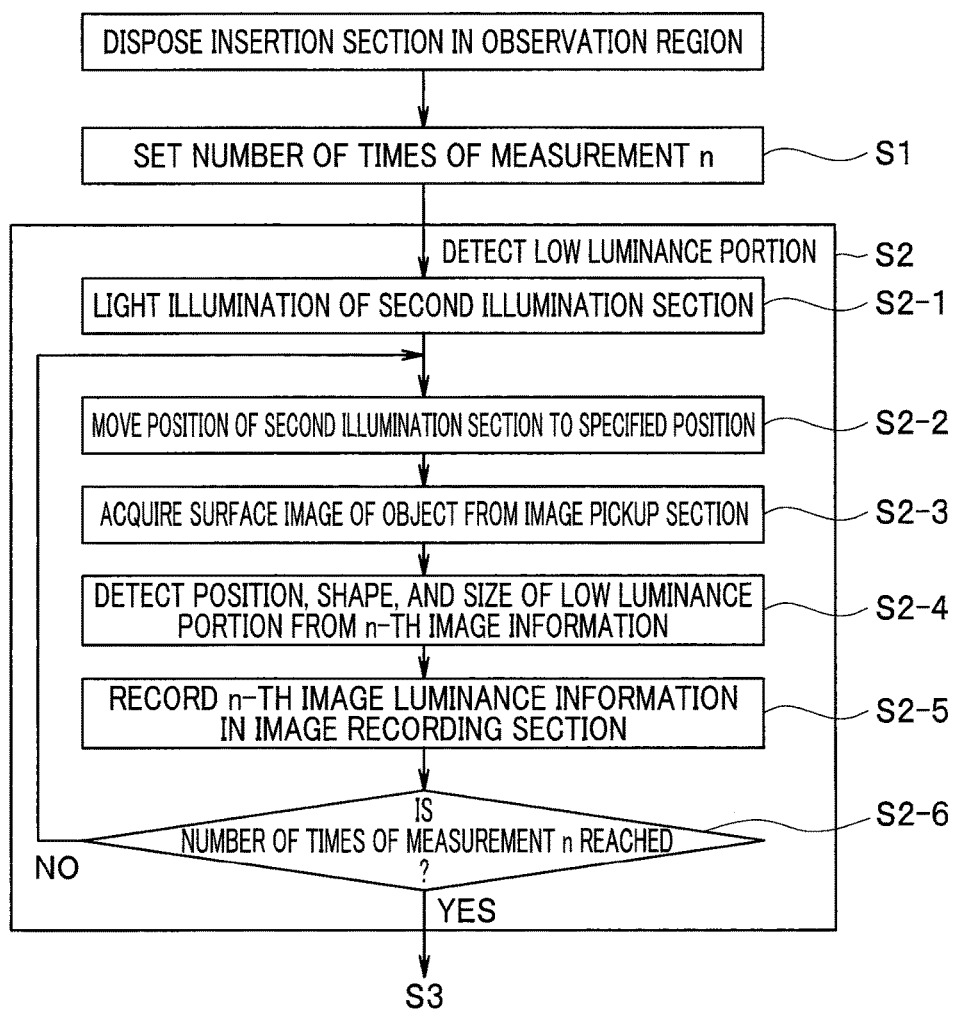
FIG. 3 is a flowchart for explaining operation in the first embodiment.
Figure 4:
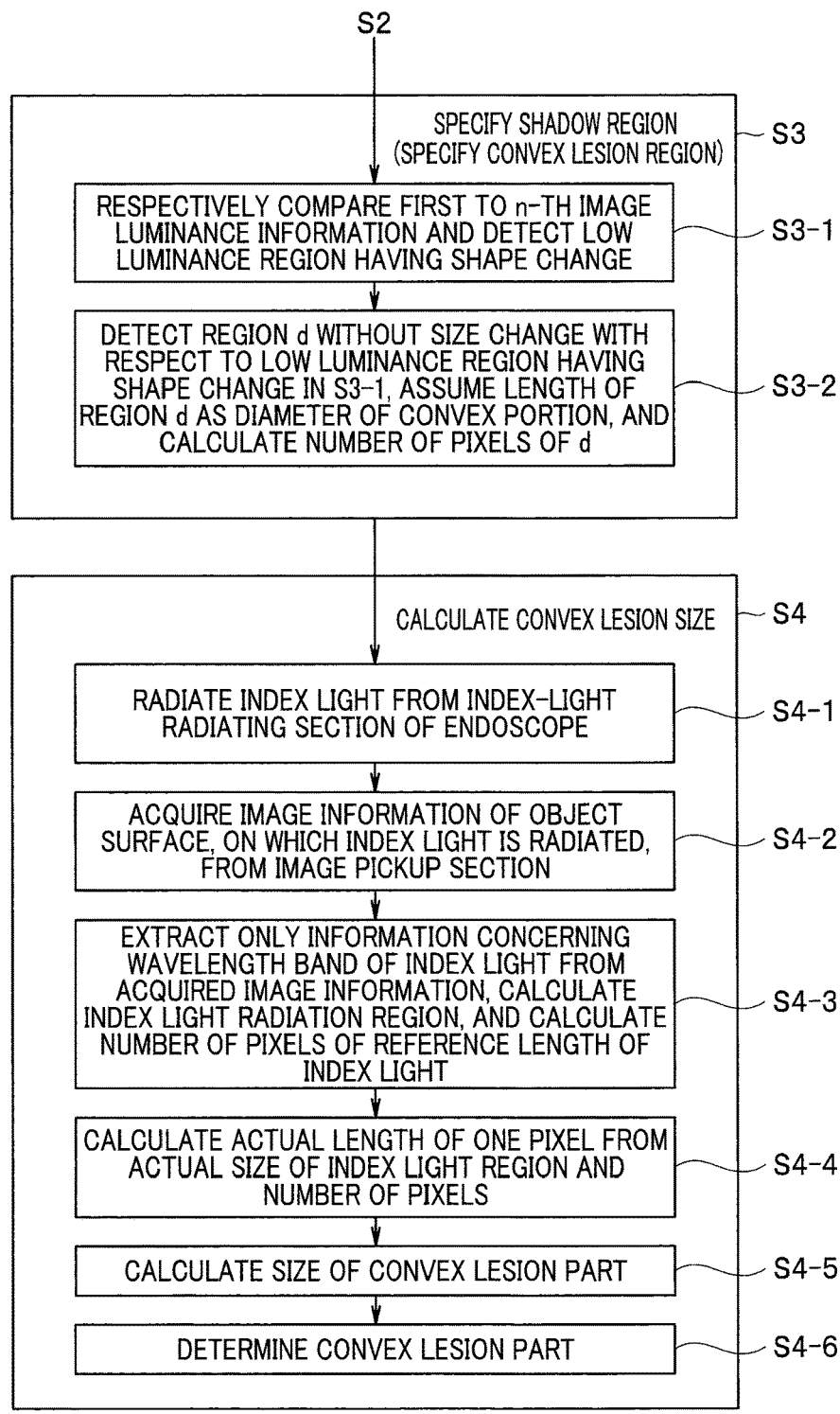
FIG. 4 is a flowchart for explaining the operation in the first embodiment.
Figure 5:
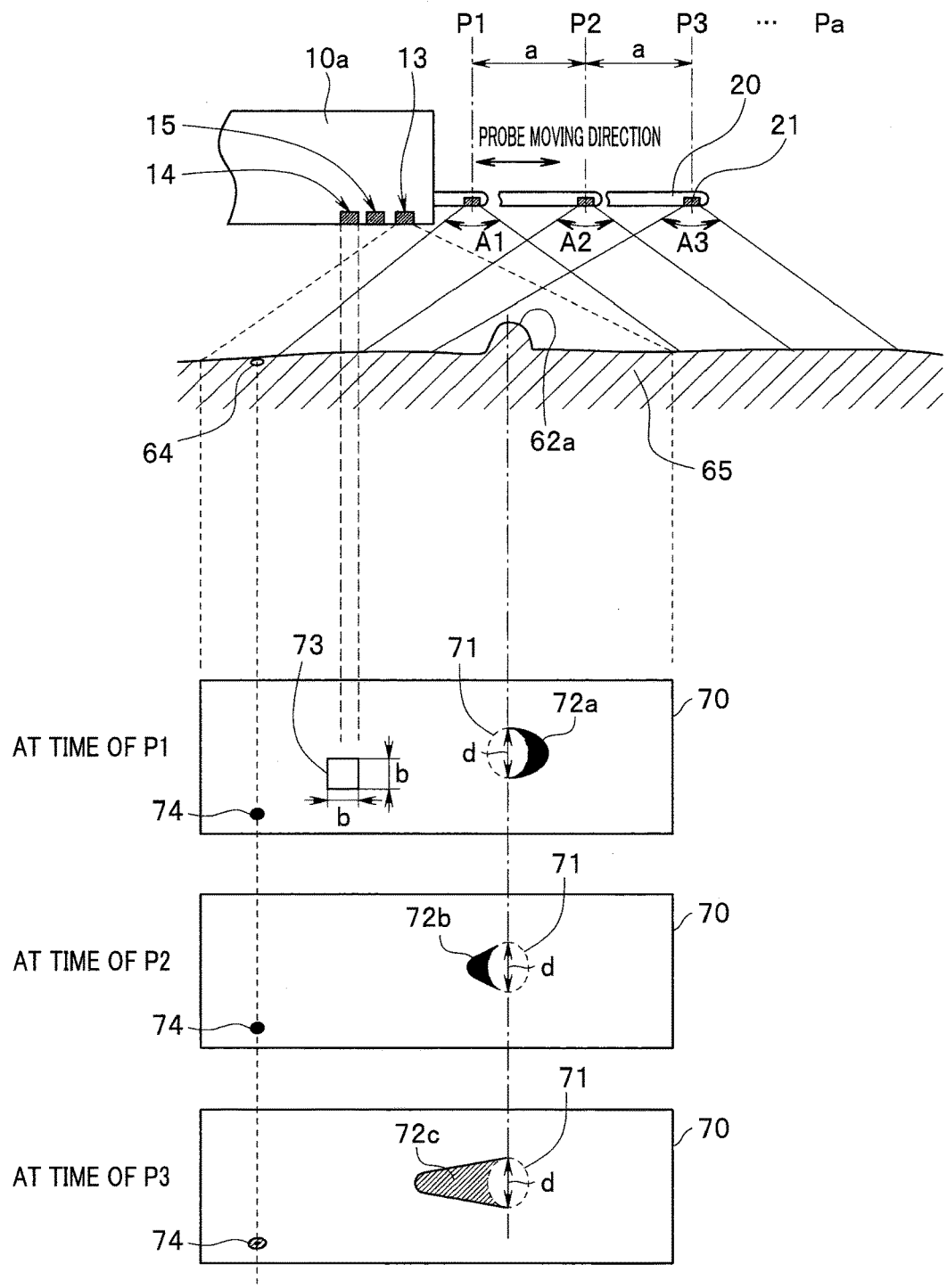
FIG. 5 is an explanatory diagram for explaining the operation in the first embodiment.

Operation in the present embodiment configured as explained above is explained with reference to FIG. 3 to FIG. 5. FIG. 3 and FIG. 4 are flowcharts for explaining the operation in the first embodiment. FIG. 5 is an explanatory diagram for explaining the operation in the first embodiment. In FIG. 5, disposition of the insertion section 10a in the observation region 65 is shown in an upper part and picked-up images in the cases in which a position of the probe 20 is P1, P2, and P3 are shown in a lower part.

As shown in FIG. 3, first, disposition of the insertion section 10a in an observation region is performed. That is, a surgeon inserts the insertion section 10a into the body cavity and disposes the insertion section 10a near the observation region 65 as shown in FIG. 5. In an example shown in FIG. 5, an example is show in which the image pickup section 13 and the second illumination section 21 are disposed on a side surface of the insertion section 10a or the probe 20 and respective optical axes are provided in directions substantially perpendicular to an advancing and retracting direction of the probe 20. For example, the insertion section 10a is disposed such that the advancing and retracting direction of the probe 20 is substantially parallel to a surface of the observation region 65.

During detection of a convex lesion part, a position of the insertion section 10a is fixed with respect to the observation region 65. In this state, in step S2, the processor device 40 detects a low luminance portion in the observation region 65. First, in step S1, the processor device 40 sets the number of times of measurement n (n is 2 or more) for detection of a convex lesion part. Note that FIG. 5 shows an example in which n is 3. Steps S2-2 to S2-6 in FIG. 3 are repeated three times. In step S2-1, the light-source control section 50 controls the light source 32 and lights the second illumination section 21.

Subsequently, the probe control section 41 controls the probe driving section 12. In step S2-2, the probe control section 41 advances and retracts the probe 20 to move the position of the second illumination section 21 to a specified position. For example, the probe control section 41 moves the probe 20 such that the position of the second illumination section 21 changes to an initial position P1.

Subsequently, the image pickup section 13 performs image pickup according to control by the processor device 40. The image pickup section 13 acquires a surface image of the observation region 65 in a visual field range indicated by a broken line in the upper part of FIG. 5. The convex portion 62a in the observation region 65 is located within an illumination range A1 of the second illumination section 21. An image portion of the convex portion 62a is also included in a picked-up image from the image pickup section 13.

The picked-up image of the image pickup section 13 is supplied to the image processing section 42 and the low-luminance-portion detecting section 44 of the processor device 40 (step S2-3). The image processing section 42 applies appropriate image signal processing to the picked-up image and thereafter gives the picked-up image to the display section 51. Consequently, it is possible to display the surface image of the observation region 65 on a screen of the display section 51.

The low-luminance-portion detecting section 44 captures the picked-up image from the image pickup section 13 as first image information and detects a position, a shape, and a size of a low luminance portion in the first image information (step S2-4). At the time of P1 shown in FIG. 5, a picked-up image 70 by illumination in the illumination range A1 in the case in which the second illumination section 21 is located in a specified position P1 is shown. An image 71 by the convex portion 62a is included in the picked-up image 70. Further, a shadow of the convex portion 62a is generated as a result of obliquely radiating illumination of the second illumination section 21 on the convex portion 62a. An image 72a of the shadow is also included in the picked-up image 70. An image portion of the image 72a of the shadow is detected as a low luminance portion by the low-luminance-portion detecting section 44. The low-luminance-portion detecting section 44 gives a detection result to the image recording section 45 as first image luminance information and causes the image recording section 45 to record the first image luminance information (step S2-5).

In step S6, the processor device 40 determines whether the number of times of measurement has reached the set number of times of measurement n. When the number of times of measurement has not reached the set number of times of measurement n, the processor device 40 returns the processing to step S2-2 and repeats the processing in steps S2-2 to S2-6.

In the example shown in FIG. 5, n is 3. The probe control section 41 controls the probe driving section 12 to advance and retract the probe 20 to move the position of the second illumination section 21 to a specified position P2. Note that the surgeon may be able to set the number of times of movement and a movement amount of the probe 20 as appropriate. The image pickup section 13 performs image pickup. The low-luminance-portion detecting section 44 captures a picked-up image as second image information, detects a low luminance portion, and records a detection result in the image recording section 45 as second luminance information. Similarly, the position of the second illumination section 21 is moved to a specified position P3 by the probe control section 41 and image pickup is performed. The low-luminance-portion detecting section 44 captures a picked-up image as third image information, detects a low-luminance portion, and records a detection result in the image recording section 45 as third image luminance information.

When the number of times of measurement has reached the set number of times of measurement n, the shadow-region specifying section 46 specifies a shadow region in step S3 in FIG. 4. That is, the shadow-region specifying section 46 reads out all pieces of image luminance information from the image recording section 45 and compares the pieces of image luminance information with one another to detect a low luminance region having a shape change.

The second illumination section 21 moves to the specified positions P1 to P3, whereby an illumination range of the second illumination section 21 changes to A1 to A3. In this case as well, the convex portion 62a is included in the illumination ranges A1 to A3. An image portion of the convex portion 62a is also included in a picked-up image from the image pickup section 13.

At the time of P2 shown in FIG. 5, the picked-up image 70 by illumination of the illumination range A2 in the case in which the second illumination section 21 is located in the specified position P2 is shown. Even when the second illumination section 21 has moved from the specified position P1 to the specified position P2, a positional relation between the image pickup section 13 and the convex portion 62a has not changed. Therefore, the image 71 of the convex portion 62a is picked up in the same shape and the same size in the same position in the picked-up image 70. On the other hand, a shape and a size of the shadow of the convex portion 62a generated by the illumination of the second illumination section 21 change according to the movement of the second illumination section 21. At the time of P1 shown in FIG. 5, the image 72a of the shadow of the convex portion 62a is shown as being picked up on a paper surface right side of the convex portion 62a. At the time of P2 shown in FIG. 5, an image 72b of the shadow of the convex portion 62a is shown as being picked up on a paper surface left side of the convex portion 62a.

Further, at the time of P3 shown in FIG. 5, the picked-up image 70 in the case in which the second illumination section 21 moves to a specified position P3 is shown. In the picked-up image 70, the convex portion 62a by illumination of the illumination range A3 of the second illumination section 21 and images 71 and 72c of a shadow of the convex portion 62a are included. As it is evident from comparison of the times of P2 and P3 shown in FIG. 5, a size and a shape change in the images 72b and 72c of the shadow according to a change from the illumination range A2 to the illumination range A3. The shadow-region specifying section 46 determines that a low luminance portion having such a shape change is a portion of a shadow by a convex portion and detects the portion as a low luminance region (step S3-1).

Since the probe 20 linearly advances and retracts, as shown at the times of P1 and P2 shown in FIG. 5, it is considered that length of the shadow of the convex portion 62a changes along an advancing and retracting direction of the probe 20 and does not change in a direction perpendicular to the advancing and retracting direction of the probe 20. That is, a portion where length of a low luminance region end portion does not change can be considered as being equivalent to an image portion of the convex portion 62a adjacent to the low luminance region. If a plane shape of the convex portion 62a is substantially circular, length of the portion where the length of the low luminance region end portion does not change may be considered to be a size (a diameter) of the convex portion 62a.

Therefore, in step S3-2, the shadow-region specifying section 46 detects a region not having a change in a size in the low luminance region, assumes length of the region (see FIG. 5) as a diameter d of the convex portion 62a, and calculates the diameter d according to, for example, the number of pixels of an image. The shadow-region specifying section 46 outputs information concerning the low luminance region and the number of pixels corresponding to the diameter d to the size comparing section 49.

Subsequently, in step S4, the processor device 40 determines, according to the diameter d, whether the size of the convex portion 62a is a size within a specified range. For the determination, the index-light-radiation control section 48 of the convex-lesion-size calculating section 47 controls the light source 32 to radiate index light from the index-light radiating section 14 on the surface of the observation region 65 (step S4-1). The index light is radiated in a specified size on the surface of the observation region 65. Note that the index-light radiating section 14 may limit a band of the index light to a predetermined band such that the index light can be surely observed on the surface of the observation region 65. Note that it is assumed that the band of the index light is different from a band of the illumination light from the second illumination section 21. When illumination light (white light) in the same band as the illumination light of the second illumination section 21 is used as the index light, the index light is radiated after the second illumination section 21 is extinguished.

In this state, the image pickup section 13 is controlled by the processor device 40 to perform image pickup (step S4-2). At the time of P1 shown in FIG. 5, an image 73 in a region of the index light radiated on the surface of the observation region 65 (an index light radiation region) is shown as being picked up. Note that, at the time of P1 shown in FIG. 5, the image 70 in the case in which the second illumination section 21 is located in the specified position P1 is shown. However, the radiation of the index light may be performed at any timing. That is, the processing in steps S4-1 to S4-4 in FIG. 4 may be carried out at other timings.

The picked-up image from the image pickup section 13 is supplied to the size comparing section 49. An image portion illuminated by the index light is also included in the picked-up image from the image pickup section 13. The size comparing section 49 calculates the number of pixels of this image portion (step S4-3). Note that, in this case, the size comparing section 49 may extract information concerning a wavelength band of the index light and calculate an image portion of the index light radiation region.

The index light is parallel light. A size of the index light radiation region of the index light radiated on the surface of the observation region 65 is known. The size comparing section 49 calculates actual length of one pixel on the basis of an actual size of the index light radiation region and the number of pixels of an image in the index light radiation region (step S4-4). For example, when the actual size of the index light radiation region is represented as b and the number of pixels of the index light radiation region is represented as β, the size comparing section 49 calculates actual length y of one pixel according to y=β/b.

Subsequently, the size comparing section 49 calculates an actual size of the convex portion 62a on the basis of the number of pixels corresponding to the diameter d of the convex portion 62a calculated in step S3-2 and the actual size y of one pixel. For example, when the number of pixels corresponding to the diameter d is represented as α, the size comparing section 49 calculates the diameter d of the convex portion 62a according to d=α·y.

In the next step S4-6, the size comparing section 49 determines, according to whether the size d of a convex lesion part is a size within a specified range, whether the convex lesion part is a convex lesion part that should be detected. The size comparing section 49 outputs a determination result concerning whether the convex lesion part is the convex lesion part that should be detected. For example, the determination result is supplied to the display section 51. Display indicating whether the convex portion 62a is the convex lesion part that should be detected, display indicating that the convex portion 62a is the convex lesion part, and the like are performed.

Note that the size comparing section 49 may directly give information concerning the size d of the convex lesion part to the display section 51 and cause the display section 51 to display indication indicating a size of the convex lesion part on the screen of the display section 51.

As shown at the times of P1 to P3 shown in FIG. 5, in the picked-up image 70, an image 74 corresponding to a very small convex portion 64 is also picked up. When a size of the convex portion 64 is a size smaller than a specified range, it is determined that the convex portion 64 is a convex portion that does not need to be detected. A detectable low luminance portion sometimes is not generated in the very small convex portion 64. Alternatively, it is conceivable that a change of a low luminance portion of the very small convex portion 64 is sufficiently small. In this case, the convex portion 64 is not determined as a low luminance region.

As explained above, in the present embodiment, it is possible to surely detect a convex portion by performing image pickup while controlling a relative positional relation between the image pickup section and the illumination section. It is determined by index light radiation whether the detected convex portion is a convex portion, a size of which is within a predetermined size range. It is possible to detect only a convex portion that should be specified as a lesion part and inform the surgeon of the convex portion.

Second Embodiment

Figure 6:
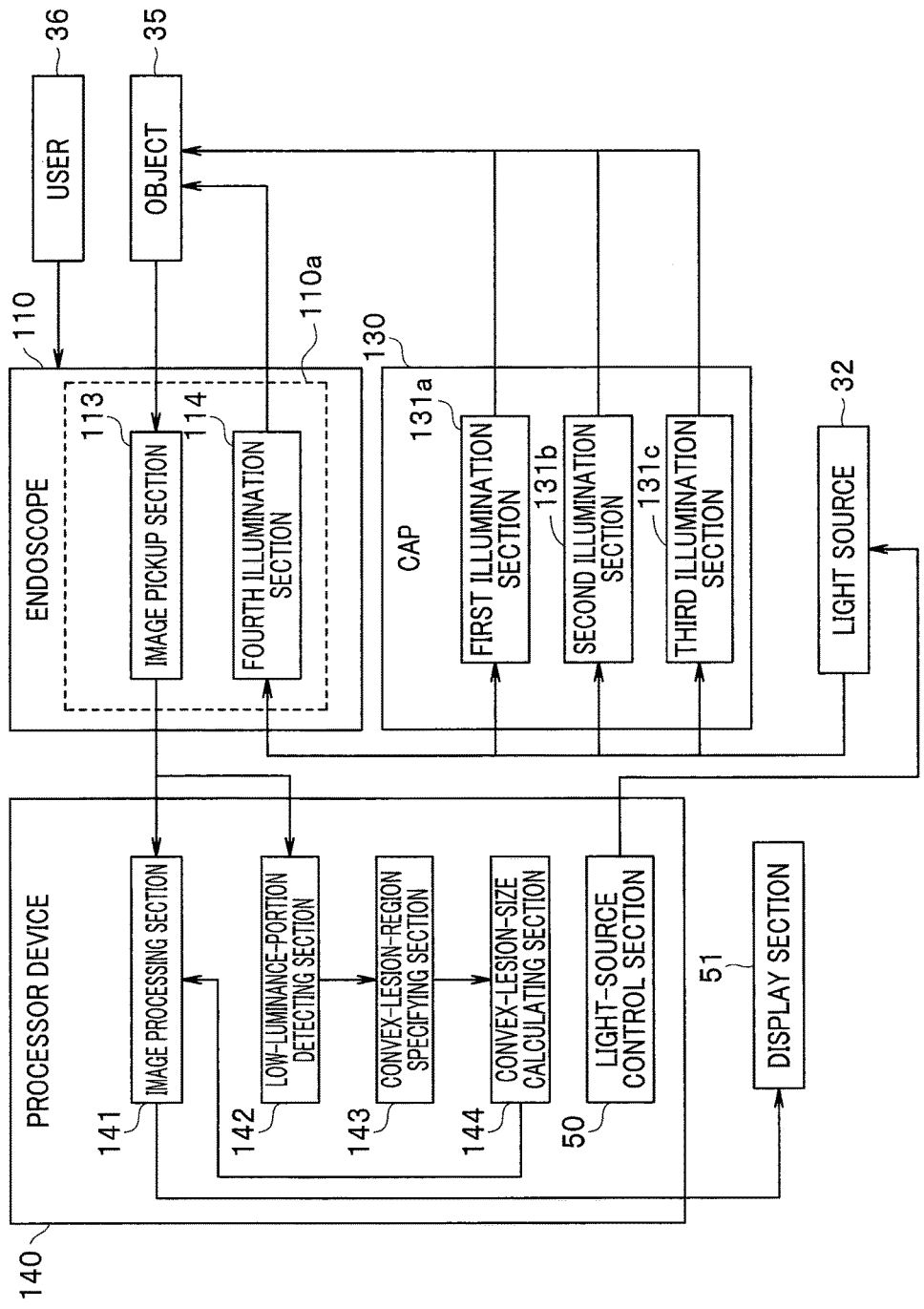
FIG. 6 is a block diagram showing a second embodiment of the present invention.

FIG. 6 is a block diagram showing a second embodiment of the present invention. In FIG. 6, components same as the components in FIG. 1 are denoted by the same reference numerals and sings and explanation of the components is omitted. In the first embodiment, the example is explained in which image pickup is performed while relatively moving the image pickup section and the illumination section, a convex portion is detected according to a shadow of the convex portion in a picked-up image, and a size of the convex portion is calculated. It is also conceivable that the shadow by the convex portion is not generated depending on a state of a surface of a biological tissue, a radiation position of illumination light, and the like. Therefore, in the present embodiment, cap-like lighting equipment is used to generate a shadow by a convex portion and detection of the convex portion and detection of a size of the convex portion are surely performed.

Figure 7:
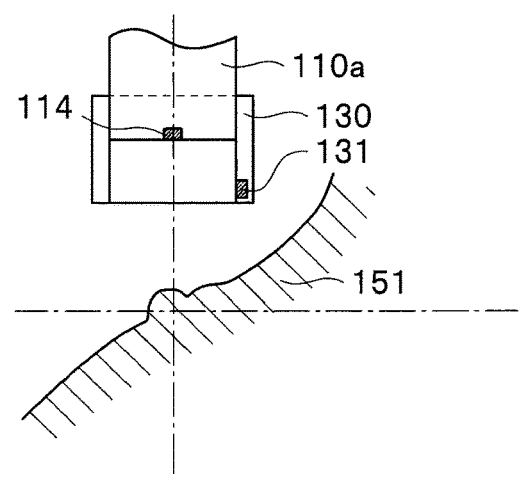
FIG. 7 is an explanatory diagram for explaining a form of use of an endoscope system in the second embodiment.
Figure 8:
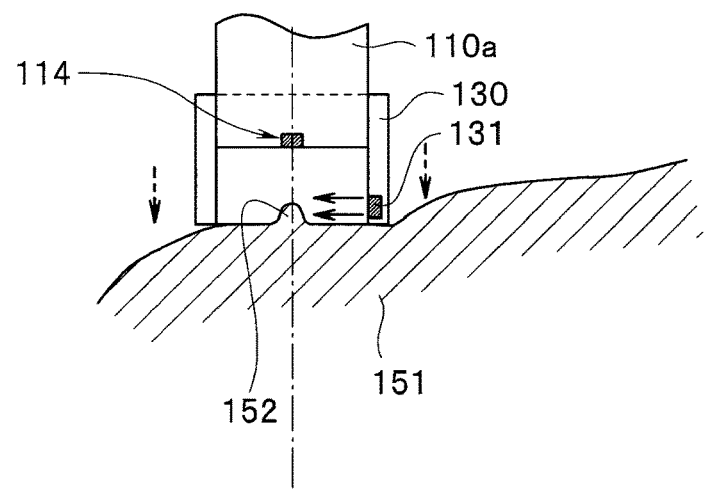
FIG. 8 is an explanatory diagram for explaining a state of use of the endoscope system in the second embodiment.

FIG. 7 and FIG. 8 are explanatory diagrams for explaining a form of use of an endoscope system in the present embodiment. FIG. 7 shows a state in which an observation region 151 is observed by an insertion section 110a of an endoscope 110 mounted with a cap 130, which is lighting equipment. A surface of the observation region 151 inclines with respect to a direction of a distal end of the insertion section 110a. Even if illumination light is radiated on the observation region 151 and a shadow, which is a low luminance portion, is observed, it is not always possible to surely detect a convex portion and a size of the convex portion from a state of the shadow.

Therefore, in the present embodiment, a direction of the insertion section 110a is set to a specified angle, e.g., parallel (or perpendicular) with respect to the surface of the observation region 151, whereby a shadow is surely generated in a convex portion by illumination light. The cap 130 is formed in, for example, a cylindrical shape opened on a distal end side. The distal end of the insertion section 110a is fit on a proximal end side. As shown in FIG. 8, the cap 130 is pushed in a direction indicated by a broken line arrow with the distal end of the cap 130 set in contact with the surface of the observation region 151 such that a convex portion 152 is located in the distal end opening of the cap 130. Consequently, the surface of the observation region 151 is deformed. A direction of the surface of the observation region 151 becomes substantially perpendicular to an axial direction of the insertion section 110a.

Illumination sections 131 (first to third illumination sections 131a to 131c explained below) configured by, for example, LEDs are provided on a distal end side inner circumferential surface of the cap 130. As indicated by solid line arrows in FIG. 8, the illumination sections 131 radiate illumination light toward a center side of the cap 130. In this state, an image of the observation region 151 is picked up in the endoscope 110. Detection of the convex portion 152 and detection of a size of the convex portion 152 are performed according to a state of a shadow in the picked-up image. Illumination light is radiated from a side surface side of the convex portion 152. It is possible to surely generate a shadow by the convex portion 152. It is possible to detect the convex portion 152. Note that, as the illumination sections 131, not only the LEDs but also fluorescent bodies, lenses that radiate light from a light source transmitted by a fiber cable, or the like may be adopted.

In FIG. 6, in the endoscope 110, an image pickup section 113 and a fourth illumination section 114 are provided in the insertion section 110a. The distal end of the insertion section 110a of the endoscope 110 is fit in a proximal end side opening of the cap 130. Three first to third illumination sections 131a to 131c (in the following explanation, when it is unnecessary to distinguish the individual illumination sections, the illumination sections are referred to as illumination sections 131 as described above) are provided in the cap 130. Note that, in FIG. 6, an example is shown in which the three illumination sections, that is, the first to third illumination sections 131a to 131c are provided as the illumination sections 131. However, two or more illumination sections only have to be disposed.

The cap 130 is formed in, for example, a cylindrical shape. All of the illumination sections 131 can radiate illumination light toward a center of the cap 130. In the present embodiment, the illumination sections 131a to 131c radiate illumination light in wavelength bands different from one another. For example, the illumination sections 131a to 131c respectively radiate R (red) light, G (green) light, and B (blue) light.

Figure 9:
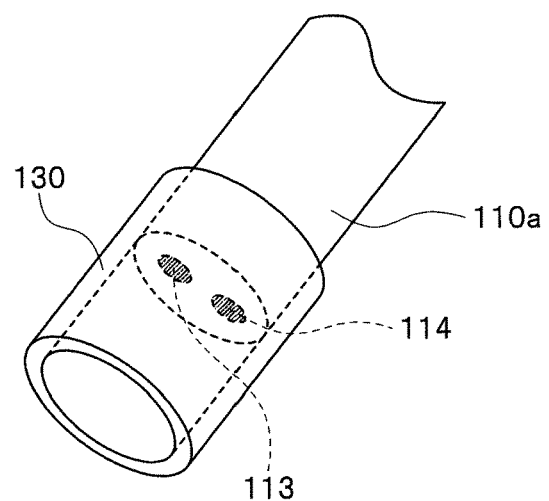
FIG. 9 is a perspective view showing a distal end of an insertion section 110$a$ to which a cap 130 is attached.
Figure 10:
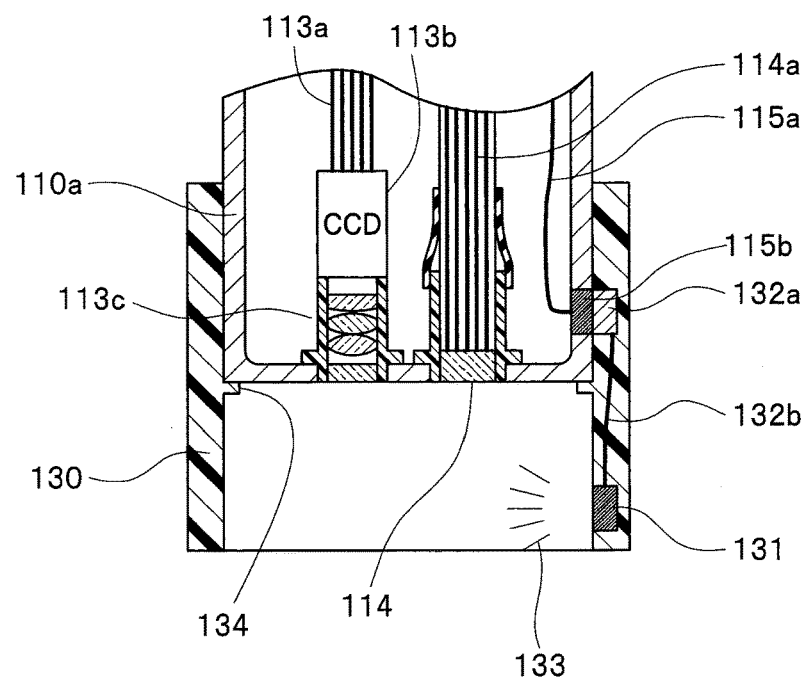
FIG. 10 is a sectional view showing a configuration of the distal end of the insertion section 110$a$ and the cap 130.

FIG. 9 is a perspective view showing a distal end of the insertion section 110a to which the cap 130 is attached. FIG. 10 is a sectional view showing a configuration of the distal end of the insertion section 110a and the cap 130. As shown in FIG. 9, the distal end of the insertion section 110a is fit in a proximal end side opening of the cylindrical cap 130 opened at both ends. As shown in FIG. 10, a convex portion 134 for positioning is provided on an inner circumferential surface of the cap 130. An insertion position of the insertion section 110a into the cap 130 is determined by being restricted by the convex portion 134.

An image pickup device 113b such as a CCD configuring the image pickup section 113 is disposed at the distal end of the insertion section 110a. A lens group 113c including a plurality of lenses is provided between the image pickup device 113b and a distal end face of the insertion section 110a. Return light from an object is focused on an image pickup surface of the image pickup device 113b via the lens group 113c. A cable 113a inserted through the insertion section 110a from the processor device 140 is connected to the image pickup device 113b. Various signals for driving the image pickup device 113b and a picked-up image obtained by the image pickup device 113b are transmitted by the cable 113a.

The fourth illumination section 114 configured by an illumination lens is disposed on the distal end face of the insertion section 110a. Light from the light source 32 led by a fiber cable 114a inserted through the insertion section 110a is radiated on the object via the fourth illumination section 114 that an emission end face of the fiber cable 114a faces. Note that the fourth illumination section 114 is used for observation of the object 35.

In the insertion section 110a in the present embodiment, an electric contact 115b is provided on a side surface on a distal end side. The electric contact 115b is connected to a signal line 115a inserted through the insertion section 110a and exposed to an outer circumferential surface of the insertion section 110a. On the other hand, an electric contact 132a is provided on the inner circumferential surface of the cap 130. When the insertion section 110a is fit in the cap 130, the electric contacts 115b and 132a come into contact with each other. The electric contact 132a is connected to the illumination section 131 via a lead wire or a signal line 132b of a flexible board or the like.

The signal line 115a is connected to the light source 32. The light source 32 can supply electric power to the illumination sections 131 via the signal line 115a, the electric contacts 115b and 132a, and the signal line 132b and control lighting of the illumination sections 131. The illumination sections 131 can radiate illumination light 133 toward the center of the cap 130.

Note that, in FIG. 10, for simplification of the drawing, an example is shown in which only one illumination section 131 is disposed. However, actually, two or more illumination sections 131 and a power supply route for driving the illumination sections 131 are configured.

The processor device 140 includes a not-shown processor such as a CPU. Respective sections in the processor device 140 can be controlled by the processor. The light-source control section 50 provided in the processor device 140 can control the light source 32 and control to individually light of the first to third illumination sections 131a to 131c provided in the cap 130.

The processor device 140 includes an image processing section 141. The image processing section 141 is configured the same as the image processing section 42 shown in FIG. 1. The image processing section 141 applies predetermined image signal processing to a picked-up image from the image pickup section 113 and thereafter gives the picked-up image to the display section 51 and causes the display section 51 to display the picked-up image.

In the processor device 140, a low-luminance-portion detecting section 142, a convex-lesion-region specifying section 143, and a convex-lesion-size calculating section 144 are provided. A picked-up image from the image pickup section 113 is given to the low-luminance-portion detecting section 142. The low-luminance-portion detecting section 142 detects a low luminance portion in a picked-up image for each of bands of the respective illumination sections 131. The convex-lesion-region specifying section 143 specifies a convex lesion region on the basis of a detection result of the low-luminance-portion detecting section 142. The convex-lesion-size calculating section 144 calculates an actual size of a convex lesion part on the basis of the specified convex lesion region.

The convex-lesion-size calculating section 144 outputs a calculation result to the image processing section 141. The image processing section 141 can cause, on the basis of the calculation result of the convex-lesion-size calculating section 144, the display section 51 to display information concerning a convex lesion present in an observation region.

Figure 11:
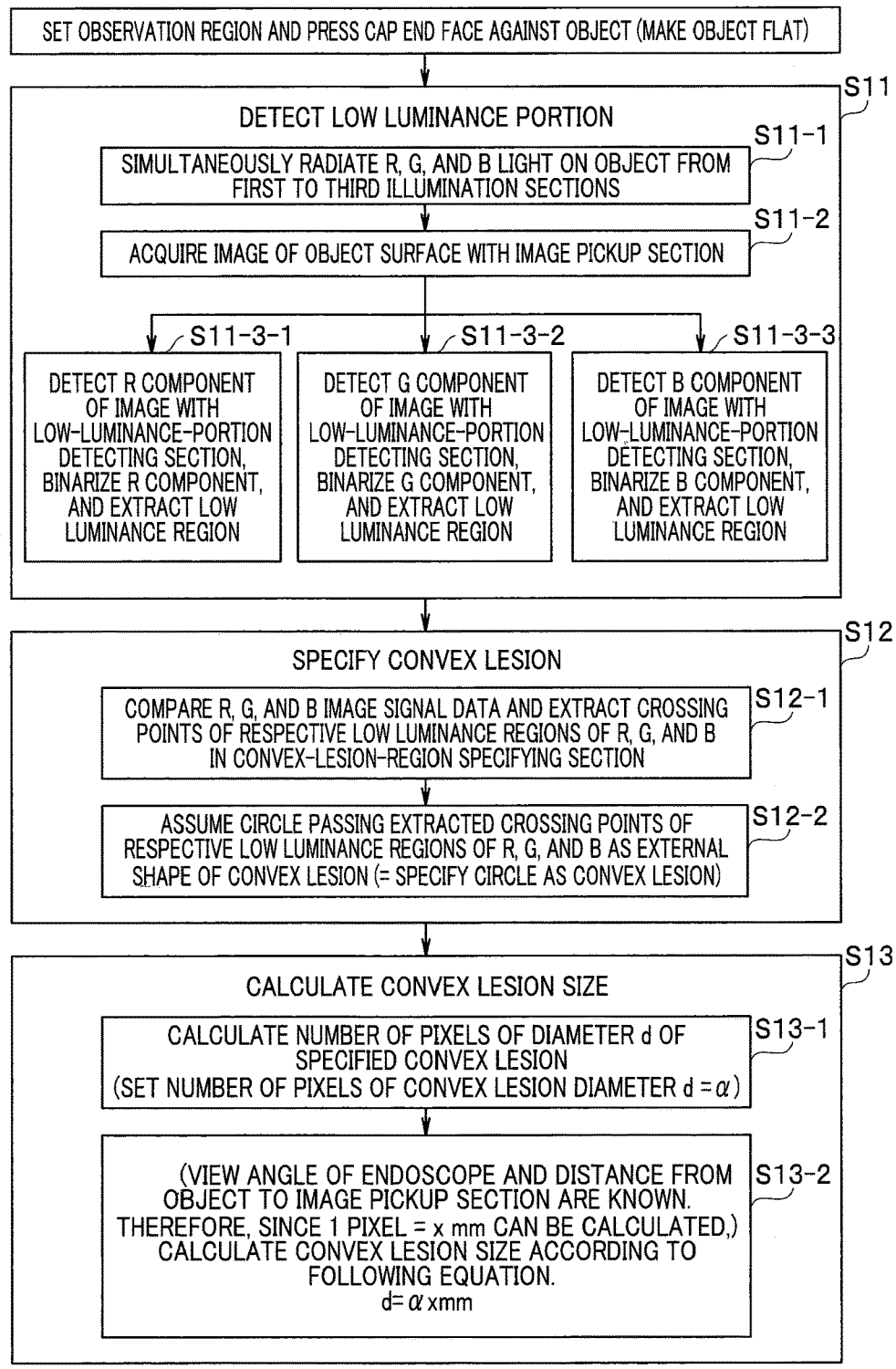
FIG. 11 is a flowchart for explaining operation in the second embodiment.
Figure 12:
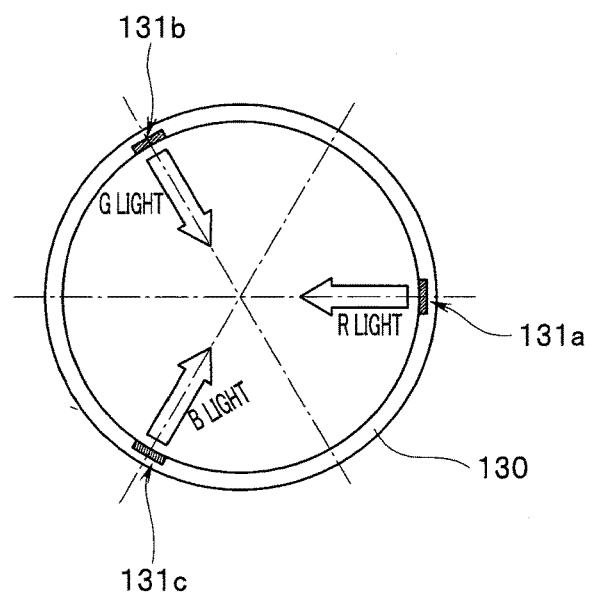
FIG. 12 is an explanatory diagram for explaining a detection method for a convex lesion part by illumination in the cap 130.
Figure 13:
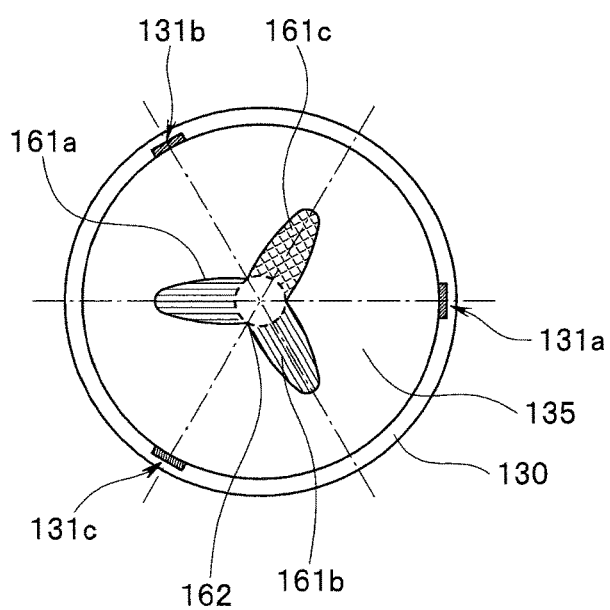
FIG. 13 is an explanatory diagram for explaining the detection method for the convex lesion part by the illumination in the cap 130.
Figure 14:
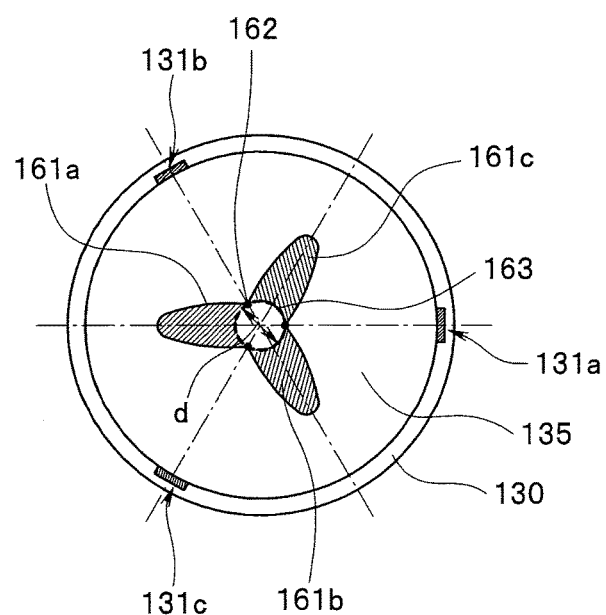
FIG. 14 is an explanatory diagram for explaining the detecting method for the convex lesion part by the illumination in the cap 130.

Operation in the embodiment configured as explained above is explained with reference to FIG. 11 to FIG. 14. FIG. 11 is a flowchart for explaining the operation in the second embodiment. FIG. 12 to FIG. 14 are explanatory diagrams for explaining a detection method for a convex lesion part by illumination in the cap 130. FIG. 12 to FIG. 14 show a state of illumination at the distal end of the cap 130 viewed from the axial direction of the insertion section 110a.

First, the insertion section 110a is disposed in a region desired to be observed. That is, the surgeon inserts the insertion section 110a, to the distal end of which the cap 130 is attached, into a body cavity and, as shown in FIG. 8, pushes in the observation region 151 with a distal end face of the cap 130. Consequently, the distal end face of the cap 130 and the surface of the observation region 151 become substantially parallel. When a convex portion is present in the observation region 151, the convex portion is illuminated from a direction perpendicular to a projecting direction of the convex portion by the illumination sections 131 disposed on the inner circumferential surface near the distal end of the cap 130.

In this state, in step S11, the processor device 140 detects a low luminance portion in the observation region 151. First, in step S11-1, the light-source control section 50 of the processor device 140 controls the light source 32 to radiate illumination light from the first to third illumination sections 131a to 131c in the cap 130. For example, it is assumed that the first to third illumination sections 131a to 131c respectively radiate R, G, and B light.

FIG. 12 shows a state of this illumination. FIG. 12 indicates that the R light, the G light, and the B light are emitted, with directions of arrows set as optical axes, from the three illumination sections 131a to 131c disposed at a predetermined angle interval (e.g., respectively at the same angle interval of 120 degrees) on the inner circumferential surface of the cap 130.

Subsequently, the image pickup section 113 performs image pickup according to the control by the processor device 140. The image pickup section 113 acquires an image of the surface of the observation region 151 surrounded by the cap 130 (step S11-2). A picked-up image from the image pickup section 113 is supplied to the image processing section 141 and the low-luminance-portion detecting section 142 of the processor device 140. The image processing section 141 applies appropriate image signal processing to the picked-up image and thereafter gives the picked-up image to the display section 51. Consequently, it is possible to display a display image of the observation region 151 on the screen of the display section 51.

The low-luminance-portion detecting section 142 detects an R component from the picked-up image from the image pickup section 113 and binarizes the R component using a predetermined threshold to extract a low luminance region (step S11-3-1). Similarly, in steps S11-3-2 and S11-3-3, the low-luminance-portion detecting section 142 respectively detects a G component and a B component from the picked-up image from the image pickup section 113 and binarizes the G component and the B component respectively using predetermined thresholds to extract low luminance regions of the respective components. In the low-luminance-portion detecting section 142, extraction results of the low luminance regions of the R, G, and B components are supplied to the convex-lesion-region specifying section 143. In step S12, the convex-lesion-region specifying section 143 specifies a convex lesion region on the basis of an output of the low-luminance-portion detecting section 142.

The illumination sections 131 radiate light in a direction substantially parallel to the surface of the observation region 151 from a position near the distal end of the cap 130 in a space 135 surrounded by the inner circumferential surface of the cap 130. Therefore, when a convex portion projecting from the surface of the observation region 151 is present, a shadow by the convex portion is considered to be surely generated by the illumination of the illumination sections 131. In other words, it can be determined that a low luminance region in a surface image is due to the shadow of the convex portion.

In FIG. 13, low luminance regions in the case in which a convex portion is present in the center of the cap 130 are indicated by hatching. A low luminance region 161a is due to a shadow of the convex portion by illumination of the second illumination section 131a. A low luminance region 161b is due to a shadow of the convex portion by illumination of the first illumination section 131b. A low luminance region 161c is due to a shadow of the convex portion by illumination of the third illumination section 131c. Illumination light of the first to third illumination sections 131a to 131c are respectively R, G, and B light. Therefore, the low luminance region 161a is considered to be based on a shadow of a cyan color excluding the R light from the first illumination section 131a among the R, G, and B light. Similarly, the low luminance region 161b is considered to be based on a shadow of a magenta color excluding the G light from the second illumination section 131b among the R, G, and B light. The low luminance region 161c is considered to be based on a shadow of a yellow color excluding the B light from the third illumination section 131c among the R, G, and B light.

The convex-lesion-region specifying section 143 extracts, on the basis of an extraction result of the low-luminance-portion detecting section 142, a crossing point 162 of the low luminance regions 161a to 161c, that is, low luminance regions where the R, G, and B components respectively decrease (step S12-1). Subsequently, in step S12-2, as shown in FIG. 14, the convex-lesion-region specifying section 143 assumes that a circle 163 passing the crossing point 162 of the low luminance regions of the R, G, and B components is an external shape of a convex lesion region. The convex-lesion-region specifying section 143 outputs information concerning the circle 163 assumed as the external shape of the convex lesion region to the convex-lesion-size calculating section 144.

In step S13, the convex-lesion-size calculating section 144 calculates a size of the convex lesion part. That is, in step S13-1, the convex-lesion-size calculating section 144 calculates the number of pixels of the diameter d of the circle 163 assumed as the convex lesion part.

Subsequently, in step S13-2, the convex-lesion-size calculating section 144 calculates actual length of one pixel of a picked-up image. Since the cap 130 is attached to the distal end of the insertion section 110a to perform image pickup, a distance from the image pickup section 113 to an object is known. A view angle of the image pickup section 113 is also known. Characteristics of the lens group 113c are also known. Therefore, the convex-lesion-size calculating section 144 can calculate actual length of one pixel of the picked-up image. Note that, since an inner diameter of the cap 130 is also known, the convex-lesion-size calculating section 144 may calculate the actual length of one pixel from the number of pixels of the inner diameter of the cap 130. In this way, in the present embodiment, it is possible to calculate the actual length of one pixel of the picked-up image without radiating index light.

The convex-lesion-size calculating section 144 calculate actual length of the diameter d of the convex lesion part from the number of pixels of the diameter d of the convex lesion part calculated in step S13-1 and the actual length of one pixel. For example, when the number of pixels of the diameter d of the convex lesion part is represented as a and the actual length of one pixel is represented as x mm, the convex-lesion-size calculating section 144 can calculate the diameter d of the convex lesion part according to d=a·x mm.

The convex-lesion-size calculating section 144 determines, according to whether the size d of the convex lesion part is a size within a specified range, whether the convex lesion part is a convex lesion part that should be detected. The convex-lesion-size calculating section 144 outputs a determination result concerning whether the convex lesion part is the convex lesion part that should be detected. For example, the determination result is supplied to the display section 51 via the image processing section 141. Display indicating whether the convex portion observed in the cap 130 is the convex lesion part that should be detected, display indicating that the convex portion is the convex lesion part, and the like are performed.

As explained above, in the present embodiment as well, it is possible to obtain effects same as the effects in the first embodiment. In the present embodiment, a cap is attached to the distal end of the insertion section and an inside of the cap is illuminated by a plurality of illumination sections provided in the cap. Consequently, when a convex portion is present in the cap, a shadow by the convex portion is surely generated. By observing a low luminance region corresponding to the shadow, it is possible to surely detect a convex lesion part in a specified size range.

(Modifications)

Figure 15:
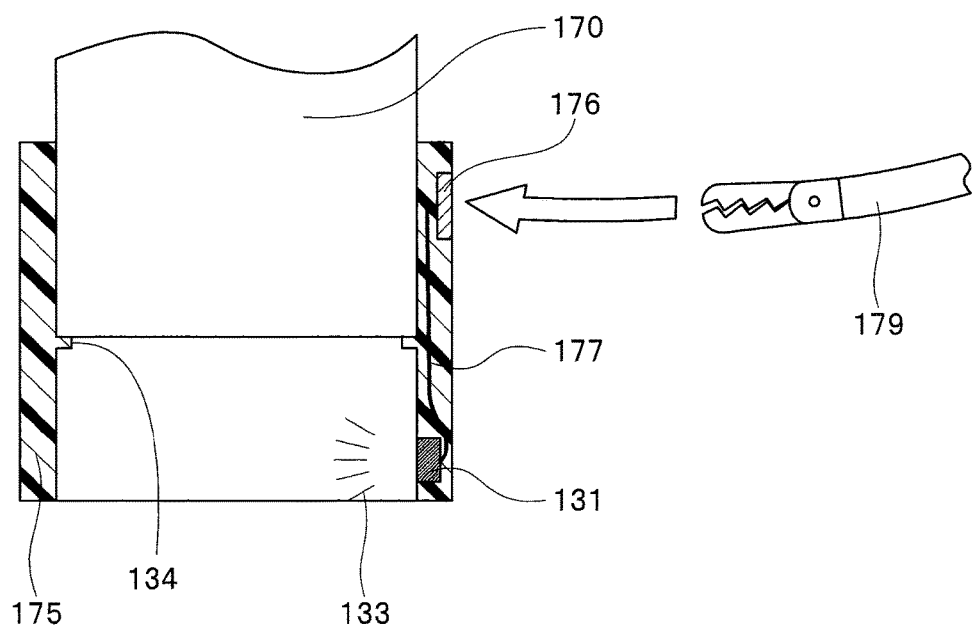
FIG. 15 is a sectional view showing a modification of the insertion section and the cap adoptable in the second embodiment.
Figure 16:
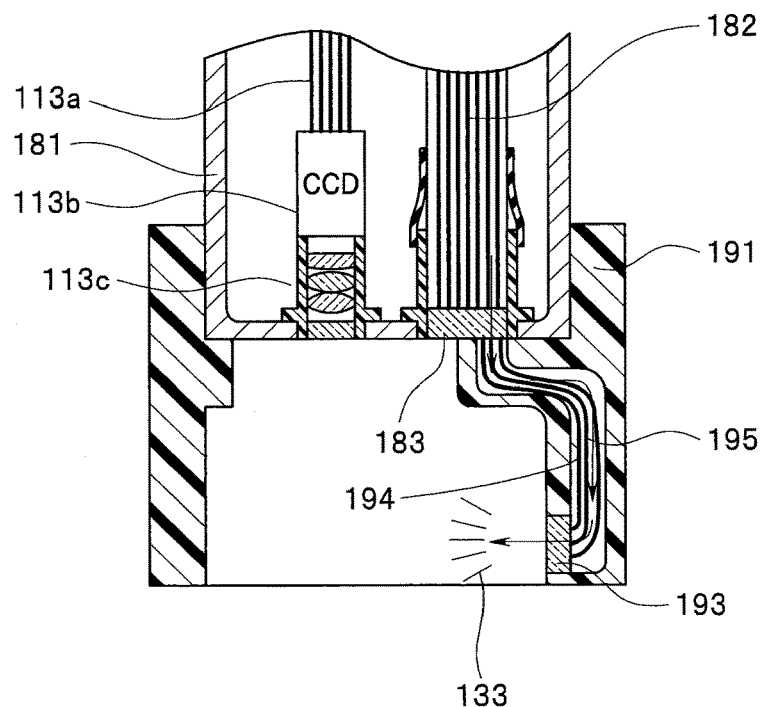
FIG. 16 is a sectional view showing a modification of the insertion section and the cap adoptable in the second embodiment.
Figure 17:
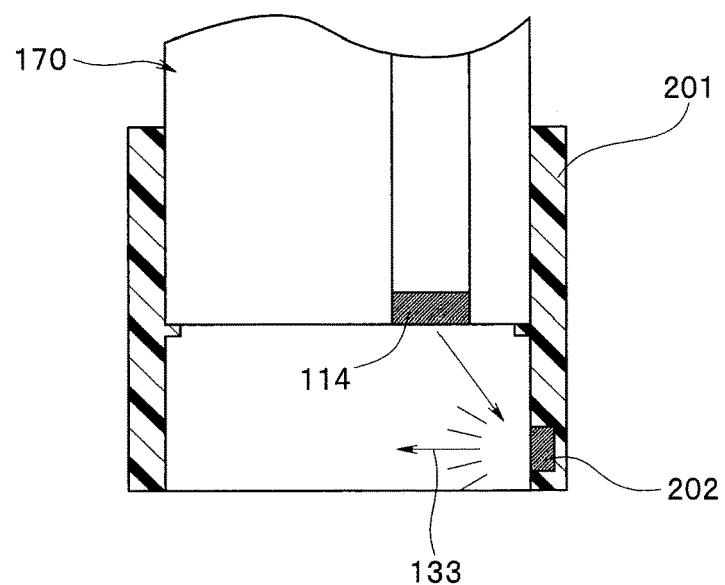
FIG. 17 is a sectional view showing a modification of the insertion section and the cap adoptable in the second embodiment.

FIG. 15 to FIG. 17 are sectional views showing modifications of the insertion section and the cap adoptable in the second embodiment.

In FIG. 15, illustration of the image pickup section 113 and the fourth illumination section 114 is omitted. An insertion section 170 shown in FIG. 15 includes a configuration same as the configuration of the insertion section 110a shown in FIG. 10 except that the electric contact 115b is omitted and the signal line 115a connected to the electric contact 115b is not inserted through. A cap 175 is different from the cap 130 shown in FIG. 10 in a power supply route to the illumination sections 131. An electric contact 176 is provided on an outer circumferential surface of the cap 175. The electric contact 176 and the illumination sections 131 are connected by a signal line 177.

In such a configuration, a bipolar forceps 179 such as a high-frequency cautery is brought into contact with the electric contact 176 and energized. Consequently, it is possible to supply electric power from the bipolar forceps 179 of the high-frequency cautery to the illumination sections 131 via the electric contact 176 and the signal line 177 and light the illumination sections 131.

FIG. 16 shows an example in which the illumination sections 131 are configured by illumination lenses. Like the insertion section 110a, an insertion section 181 shown in FIG. 16 includes the cable 113a, the image pickup device 113b, and the lens group 113c. In the insertion section 181, a lens 183 configuring the fourth illumination section 114 is disposed on a distal end face. A fiber cable 182 for guiding light from the light source 32 is disposed in the insertion section 181. An emission end face of the fiber cable 182 faces the lens 183. The light guided by the fiber cable 182 is emitted from the lens 183.

On the other hand, on an inner circumferential surface near a distal end of a cap 191, a lens 193, a light emission surface of which is exposed on the inner circumferential surface, is disposed. In the cap 191, a sidewall is formed thick. A light guide path 194 is formed in the side wall. An opening section at one end of the light guide path 194 faces a part of an emission surface of the lens 183. An opening section at the other end faces the lens 193. A fiber cable 195 is disposed in the light guide path 194. A part of light emitted from the lens 183 is emitted from the lens 193 via the fiber cable 195 in the light guide path 194 as indicated by an arrow.

In FIG. 17, illustration of the image pickup section 113 is omitted. The insertion section 170 shown in FIG. 17 includes a configuration same as the configuration of the insertion section 110a shown in FIG. 10 except that the electric contact 115b is omitted and the signal line 115a connected to the electric contact 115b is not inserted through. In a cap 201, a light accumulating body or a fluorescent body is used as an illumination section 202. The illumination section 202, in which the light accumulating body is used, accumulates light from the fourth illumination section 114 and radiates the light toward a center of the cap 201 as indicated by an arrow.

(Modification)

Incidentally, a surface of an observation region is not always flat. When the surface of the observation region is not flat, it is conceivable that accuracy of detection of a convex portion based on a picked-up image and calculation of a size of the convex portion is deteriorated. Therefore, in this modification, a lattice is projected on the surface of the observation region by an illumination section (e.g., the first illumination section 15 shown in FIG. 1 or the fourth illumination section 114 shown in FIG. 6) and the picked-up image is corrected on the basis of a shape of the projected lattice to improve the accuracy of the detection of the convex portion and the calculation of the size of the convex portion.

Figure 18A:
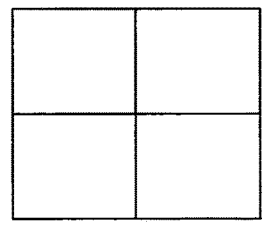
FIG. 18A is an explanatory diagram for explaining a shape of a projected lattice of an observation region.
Figure 18B:
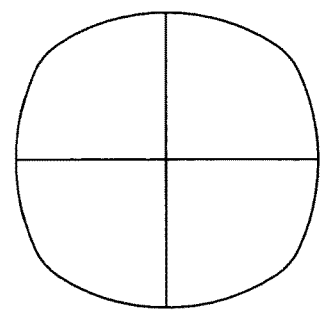
FIG. 18B is an explanatory diagram for explaining a shape of a projected lattice of the observation region.
Figure 18C:
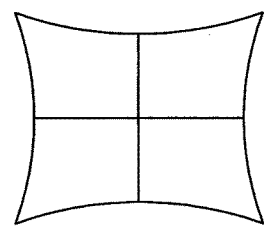
FIG. 18C is an explanatory diagram for explaining a shape of a projected lattice of the observation region.
Figure 18D:
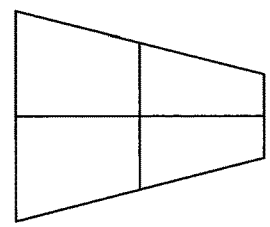
FIG. 18D is an explanatory diagram for explaining a shape of a projected lattice of the observation region.
Figure 18E:
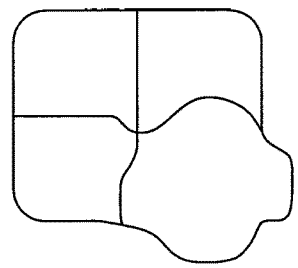
FIG. 18E is an explanatory diagram for explaining a shape of a projected lattice of the observation region.

FIGS. 18A to 18E are explanatory diagrams for explaining shapes of lattices projected on the observation region. FIG. 18A is an example in which the surface of the observation region is flat. FIG. 18B to FIG. 18E respectively show a case in which the surface of the observation region is convex, a case in which the surface of the observation region is concave, a case in which the surface of the observation region is inclined, and a case in which the surface of the observation region is partially convex.

The processor devices 40 and 140 in the embodiments are capable of improving detection accuracy of a convex shape by estimating a surface shape of an observation region on the basis of a lattice shape in a picked-up image and using a correction value based on an estimation result.

It is also possible to adopt a method of forming a surface shape flat by not only performing correction based on an estimation result of a surface shape according to image processing but also pressing an observation region.

Figure 19A:
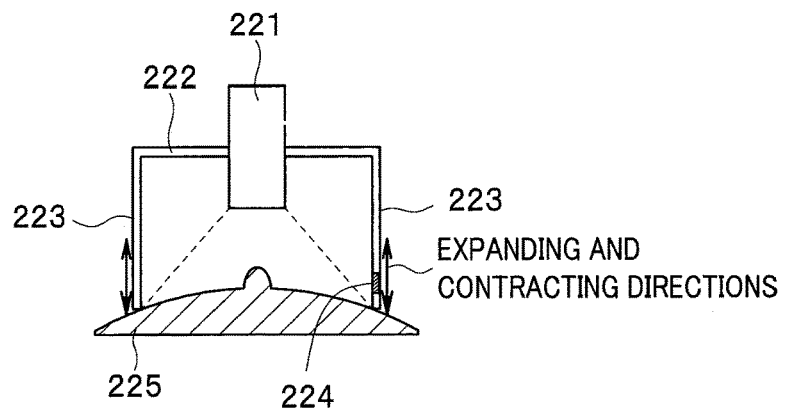
FIG. 19A is an explanatory diagram showing a modification.
Figure 19B:
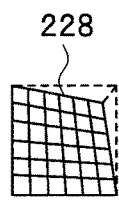
FIG. 19B is an explanatory diagram showing a modification.
Figure 19C:
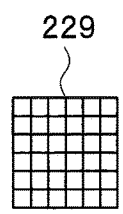
FIG. 19C is an explanatory diagram showing a modification.

FIG. 19A to FIG. 19C are explanatory diagrams showing an example of a configuration in this case. FIG. 19A shows an example of an insertion section 221 including a pressing member for an observation region. On a side surface of the insertion section 221, a plurality of claw members 223 capable of expanding and contracting in an axial direction of the insertion section 221 are disposed. The respective claw members 223 are capable of individually expanding and contracting in an expanding and contracting direction indicated by an arrow in FIG. 19A by a not-shown driving mechanism. It is possible to change a surface shape of an observation region 225 by individually controlling expanding and contracting directions and expansion and contraction amounts of the respective claw members 223.

For example, it is assumed that the observation region 225 inclines with respect to the axial direction of the insertion section 221 and a picked-up image of a lattice projected on the surface of the observation region 225 from the insertion section 221 is a distorted lattice image 228 as shown in FIG. 19B. In this case, a processor device is capable of making it possible to obtain a lattice image 229 shown in FIG. 19C by extending, for example, one of the claw members 223 to the observation region 225 side on the basis of a lattice shape of the lattice image 228. Consequently, it is possible to improve detection accuracy of a convex shape.

Since length of the claw members 223 is known and a view angle of an image pickup section provided in the insertion section 221 is also known, sizes of respective lattices of the lattice image 229 shown in FIG. 19C are known. Therefore, it is possible to calculate an actual size of a detected convex lesion part by using the lattice image 229. In this way, in the modification shown in FIG. 19A to 19C, it is possible to use the lattices as indexes for detection of a size.

Third Embodiment

Figure 20:
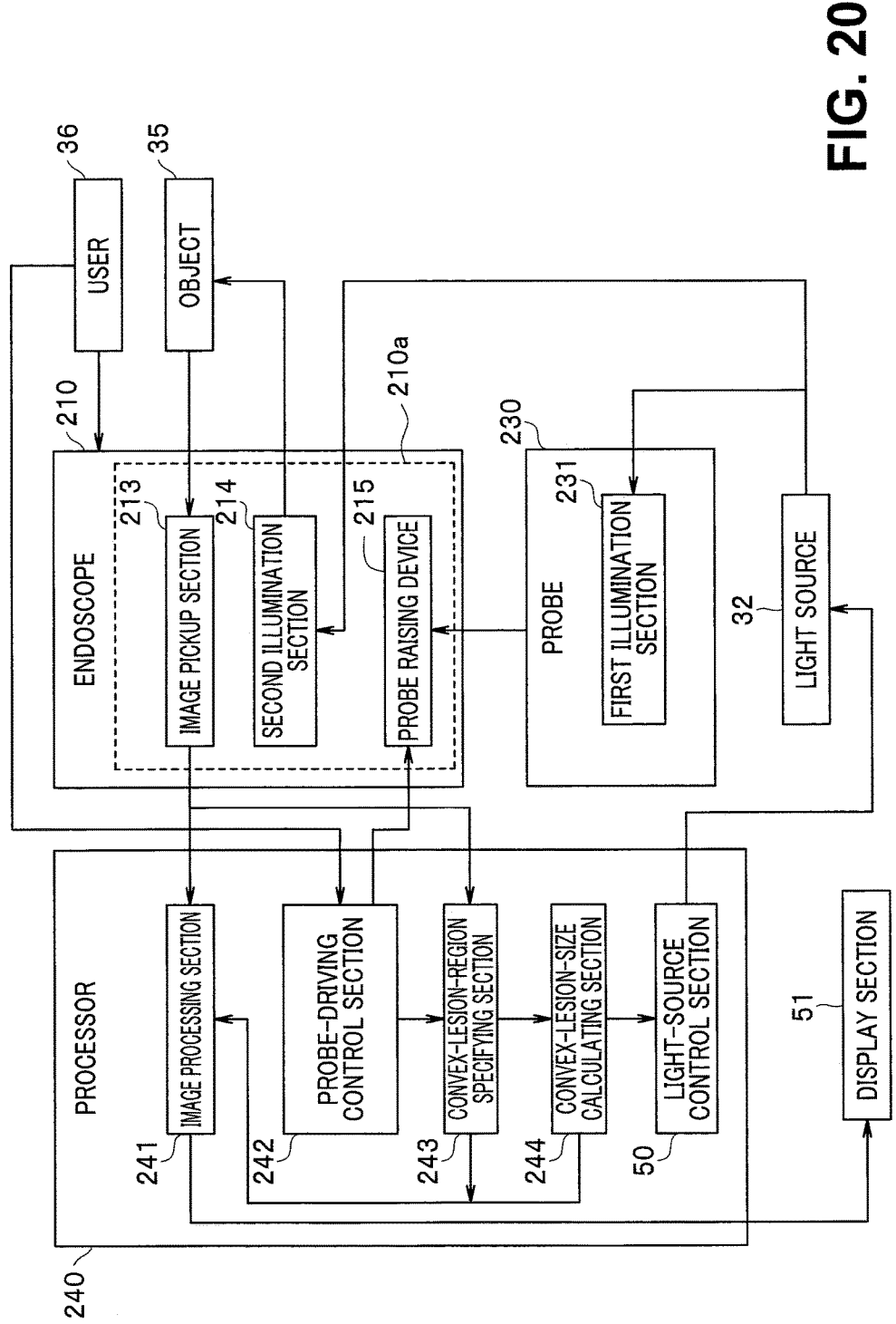
FIG. 20 is a block diagram showing a third embodiment of the present invention.

FIG. 20 is a block diagram showing a third embodiment of the present invention. In FIG. 20, components same as the components shown in FIG. 1 are denoted by the same reference numerals and signs and explanation of the components is omitted. In the embodiments explained above, the example is explained in which an object is irradiated from directions different from one another at the same time or at different times and a convex portion is detected from a state of a shadow and a size of the convex portion is calculated. In the present embodiment, a size of a convex portion is calculated by only illumination on an object from one direction. Note that the present embodiment indicates a method for calculating an accurate size of a convex portion, a position of which is known. However, it is also possible to detect the position of the convex portion by adopting a method same as the method in the embodiments explained above.

As shown in FIG. 20, an image pickup section 213, a second illumination section 214, and a probe raising device 215 are provided in an insertion section 210a of an endoscope 210. The probe raising device 215 is provided on a side surface of the insertion section 210a. A probe 230 can be projected from the probe raising device 215 and disposed in a state in which the probe 230 inclines at a predetermined angle in an axial direction of the insertion section 210a. A probe insertion port is provided in a not-shown operation section attached to a proximal end side of the insertion section 210a. The probe 230 is inserted through a channel that pierces through the insertion section 210a from the probe insertion port to the probe raising device 215. By advancing and retracting the probe 230 from the probe insertion port side and operating a not-shown operation lever provided in the operation section to drive the probe raising device 215, it is possible to freely control a projection amount and an inclination angle of the probe 230 from the insertion section 210a.

Figure 21:
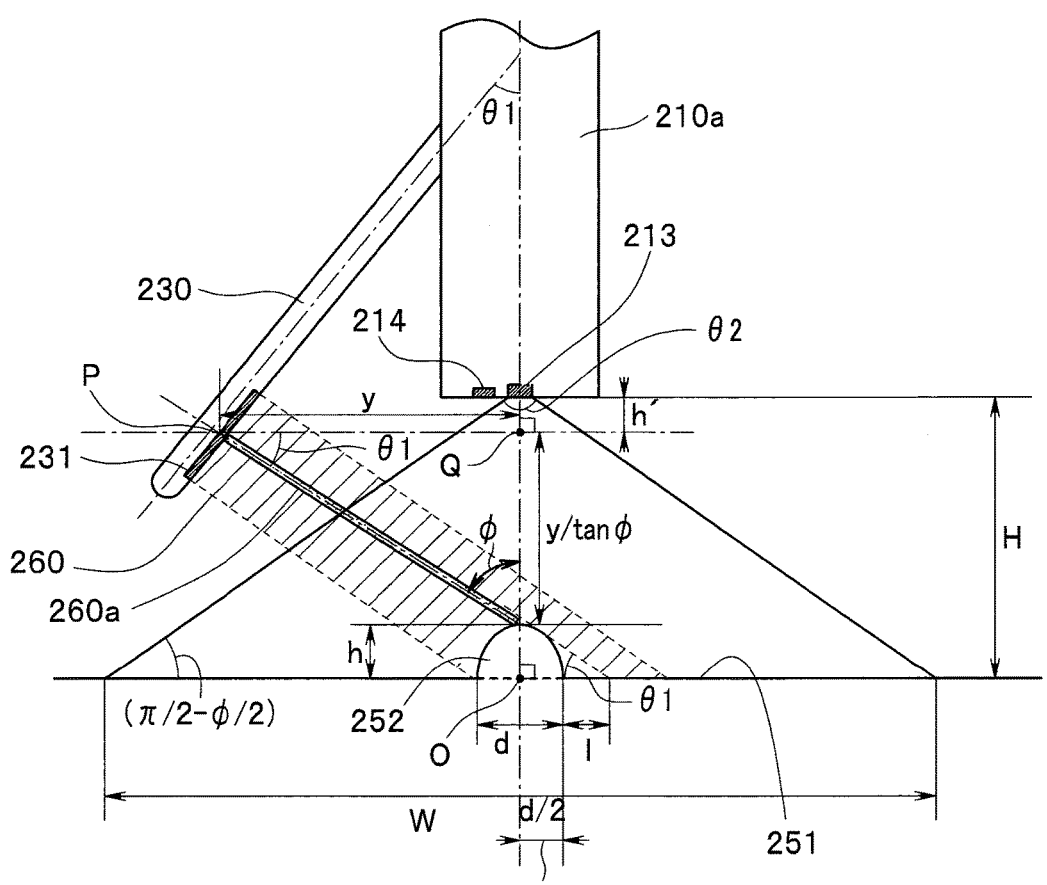
FIG. 21 is an explanatory diagram for explaining a measurement method by an endoscope system in the third embodiment.

FIG. 21 is an explanatory diagram for explaining a measurement method by an endoscope system in the present embodiment. As shown in FIG. 21, the image pickup section 213 and the second illumination section 214 are provided at a distal end portion of the insertion section 210a. The endoscope 210 can illuminate the axial direction of the insertion section 210a and pick up an image.

The probe 230 projects from the probe raising device 215 (not shown in FIG. 21) provided on a side surface of the insertion section 210a while inclining at a predetermined angle with respect to the axial direction of the insertion section 210a. A projection amount and an inclination angle of the probe 230 are known. A first illumination section 231 is disposed on a side surface on a distal end side of the probe 230. The first illumination section 231 can radiate light from the light source 32. Note that the first illumination section 231 can also be configured by an LED. In this case, electric power is supplied to the first illumination section 231, for example, from the light source 32 and light emission is controlled.

In the present embodiment, the first illumination section 231 can emit parallel light. Further, the first illumination section 231 may be capable of adjusting a size of a light beam. For example, the first illumination section 231 may be capable of emitting two kinds of light beams, that is, beam-like light obtained by sufficiently narrowing a light beam and a light beam having predetermined width.

In FIG. 21, an example is shown in which a size of a convex portion 252 formed on the surface of an observation region 251 is measured. However, the projection amount and the inclination angle of the probe 230 are set as appropriate, whereby the first illumination section 231 can illuminate the convex portion 252 obliquely with respect to a projecting direction of the convex portion 252.

A position of the convex portion 252 may be detected by a method same as the method in the second embodiment by providing, on the side surface of the insertion section 210a, a plurality of probes and a plurality of first illumination sections including configurations same as the configurations of the probe 230 and the first illumination section 231 and illuminating the convex portion 252 with light in different bands from a plurality of directions.

A processor device 240 includes a not-shown processor such as a CPU and can control respective sections in the processor device 240 with the processor. The light-source control section 50 provided in the processor device 240 controls the light source 32 and controls lighting of the first illumination section 231 and the second illumination section 214.

The processor device 240 includes an image processing section 241. The image processing section 241 includes a configuration same as the configuration of the image processing section 42 shown in FIG. 1. The image processing section 241 applies predetermined image signal processing to a picked-up image from the image pickup section 213 and thereafter gives the picked-up image to the display section 51 and causes the display section 51 to display the picked-up image.

In the processor device 240, a probe-driving control section 242, a convex-lesion-region specifying section 243, and a convex-lesion-size calculating section 244 are provided. The probe-driving control section 242 can drive the probe raising device 215 and change an inclination angle of the probe 230 on the basis of operation by the surgeon. Note that probe-driving control section 242 can change a projection amount of the probe 230 as well according to operation by the surgeon.

The convex-lesion-region specifying section 243 specifies a convex lesion region. The convex-lesion-size calculating section 244 calculates an actual size of a convex lesion part on the basis of the specified convex lesion region.

The convex-lesion-size calculating section 244 outputs a calculation result to the image processing section 241. The image processing section 241 can cause, on the basis of the calculation result of the convex-lesion-size calculating section 244, the display section 51 to display information concerning a convex lesion present in an observation region.

Figure 22:
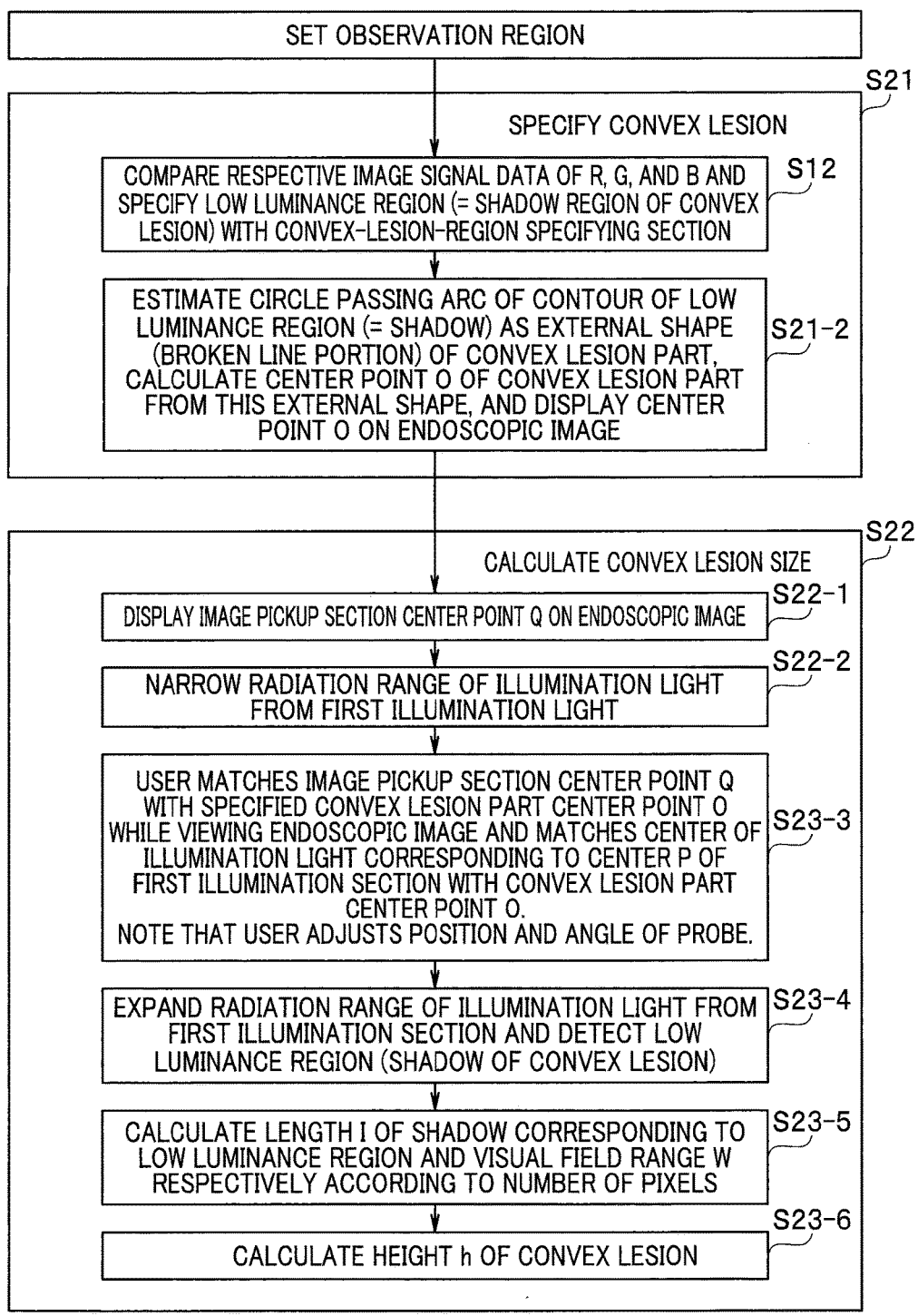
FIG. 22 is a flowchart for explaining operation in the third embodiment.
Figure 23:
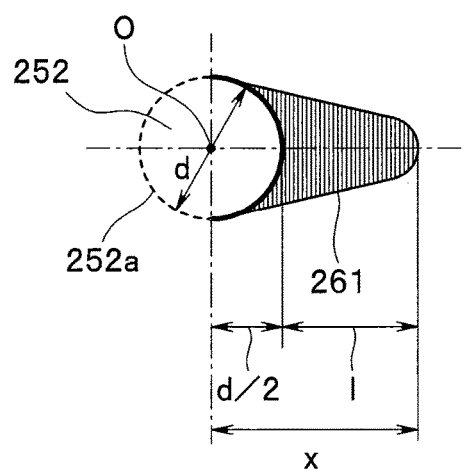
FIG. 23 is an explanatory diagram showing a state of a shadow of a convex portion in the third embodiment.

Operation in the embodiment configured as explained above is explained with reference to FIG. 21 to FIG. 23. FIG. 22 is a flowchart for explaining the operation in the third embodiment. FIG. 23 is an explanatory diagram showing a state of a shadow of a convex portion in the third embodiment.

First, the insertion section 210a is disposed in a region desired to be observed. For example, it is also possible that the observation region is illuminated by the second illumination section 214 provided at a distal end of the insertion section 210a, image pickup is performed by the image pickup section 213, the display section 51 is caused to display a picked-up image, and a surgeon observes the display of the display section 51 to specify the observation region. A convex portion may be detected by a method same as the method in the embodiments explained above. In this case, a convex lesion part can be specified. Therefore, indication indicating an external shape of the convex lesion part may be displayed in the picked-up image displayed on the display section 51.

Convex lesion specifying processing in step S21 in FIG. 22 indicates an example in which a convex lesion part is specified from a low luminance region by a method same as the method in the second embodiment (step S12). Note that, as explained above, it is possible to execute the processing in step S21 by using three probes and three first illumination sections same as the probe 230 and the first illumination section 231 as explained above.

FIG. 21 shows a state in which the insertion section 210a is fixed and disposed in a state in which the axial direction of the insertion section 210a is directed to the convex portion 252 on a surface of the observation region 251. In this state, the probe-driving control section 242 changes a projection amount and a projection angle of the probe 230 on the basis of operation by the surgeon and enables illumination on the convex portion 252 by the first illumination section 231. Subsequently, the first illumination section 231 is lit by the light-source control section 50.

FIG. 23 shows the convex portion 252 and a shadow 261 generated in the convex portion 252 in this case. An image of the convex portion 252 and the shadow 261 is picked up by the image pickup section 213. The picked-up image is given to the convex-lesion-region specifying section 143. The convex-lesion-region specifying section 143 calculates an arc (a thick line in FIG. 23) of a contour of the shadow 261 on the basis of the picked-up image and estimates a circuit passing the arc as an external shape 252a (a broken line in FIG. 23) of a convex lesion part. The convex-lesion-region specifying section 143 calculates a center point O of the estimated external shape 252a. The convex-lesion-region specifying section 143 gives information concerning the calculated center point O to the image processing section 141 and causes the image processing section 141 to display indication indicating a position of the center point O in the picked-up image.

In step S22, the convex-lesion-size calculating section 144 calculates a size of the convex lesion part. That is, in step S22-1, the convex-lesion-size calculating section 144 causes the display section 51 to display, on the displayed picked-up image, indication indicating the position of the center point Q in a visual field range of the image pickup section 113.

Subsequently, in order to calculate a size of a convex lesion, the surgeon performs fine adjustment of a position and a direction of the insertion section 210a and a projection amount and an inclination angle of the probe 230. Consequently, a positional relation between the image pickup section 213 and the convex portion 252, a visual field direction and a range of the image pickup section 213, and an illumination direction of the first illumination section 231 are specified. In order to facilitate setting of the illumination direction of the first illumination section 231, the convex-lesion-size calculating section 144 may control the light-source control section 50 and form a light beam of illumination light of the first illumination section 231 in a sufficiently thin beam shape (step S22-2).

In step S23-3, the surgeon finely adjusts, while viewing an endoscopic image displayed on the display section 51, a position of the insertion section 210a to match display of the convex lesion part center point O and display of the image pickup section center point Q. Subsequently, the surgeon finely adjusts a projection amount and an inclination angle of the probe 230 and matches a center of illumination light corresponding to the center point P of the first illumination section with a point on a surface of the convex portion 252 corresponding to the convex lesion part center point O. A light beam 260a shown in FIG. 21 indicates a beam-like light beam used during the adjustment.

Subsequently, the convex-lesion-size calculating section 144 expands an irradiation range of light from the first illumination section 231 in order to generate the shadow 261 shown in FIG. 23 (step S23-4). Consequently, the first illumination section 231 illuminates the convex portion 252 with a light beam 260 indicated by hatching in FIG. 21. In step S23-5, the convex-lesion-size calculating section 144 calculates length I of the shadow 261 according to the number of pixels of a low luminance region in the picked-up image corresponding to the shadow 261. The convex-lesion-size calculating section 144 calculates a visual field range W according to the number of pixels.

Subsequently, the convex-lesion-size calculating section 144 assumes that a shape of the convex lesion part is a semispherical shape and calculates height h of the convex lesion part as explained below using a known value (step S23-6). Note that, as shown in FIG. 21, the surface of the observation region 251 is flat. A direction perpendicular to the surface and the axial direction of the insertion section 210a coincide with each other. In the following explanation, the axial direction is set as a height direction and a direction parallel to the surface of the observation region 251 is set as a horizontal direction. In FIG. 21, meanings of signs are as follows: his convex lesion part height, H is height from the plane of the observation region 251 to the image pickup section 213, h' is a difference between height of the image pickup section 213 and height of the center point P of the first illumination section 231, d is a diameter of the convex portion 252, I is length of the shadow 261 of the convex portion 252, W is a visual field range (diagonal) by the image pickup section 213, y is a distance in the horizontal direction between the center point P of the first illumination section 231 and the center Q of the image pickup section 213, θ1 is an inclination angle of the probe 230 (an angle formed by the center axis of the insertion section 210a and a center axis of the probe 230), θ2 is a view angle of the image pickup section 213, and φ is an angle formed by an optical axis of the image pickup section 213 and an illumination direction of the first illumination section 231.

When a distance from a center of the convex portion 252 (the center point O of the convex lesion part) to a distal end of the shadow 261 is represented as x, since an angle formed by illumination light from the first illumination section 231 with respect to the horizontal direction is θ1 as shown in FIG. 21, x=h/tan θ1 holds. Therefore, I=x−(d/2)=(h/tan θ1)−(d/2). A sufficiently small size of, for example, approximately 2 mm or less is assumed as the convex portion 252. When d is approximated as d=0, the following Equation (1) is obtained:

$$h = I \cdot \tan θ1 \quad (1)$$

The angle φ is φ=(π/2)−θ1 and is a known value. The height H is indicated by the following Equation (2) using the angle φ and unknown values h and h':

$$H = h + y/\tan φ + h' \quad (2)$$

When Equation (2) is substituted in Equation (1), the following Equation (3) is obtained:

$$H = I \cdot \tan θ1 + (y/\tan φ) + h' \quad (3)$$

Since the view angle θ2 of the image pickup section 213 is a known value, a relation between the visual field range W and the height H is also known. Therefore, the visual field range W is represented by a function of the height H indicated by the following Equation (4):

$$W = f(H) \quad (4)$$

Since the view angle of the image pickup section 213 is θ2, H·tan(θ2/2)=W/2 and the following Equation (5) is obtained:

$$W = 2H \cdot \tan(θ2/2) \quad (5)$$

It is assumed that I/W=K. Since the numbers of pixels of I and W have been calculated, K is a known value. I/W=K is transformed as W=I/K and the following Equation (6) is obtained using Equation (3) and Equation (4) above:

$$W = I/K = f(I \cdot \tan θ1 + (y/\tan φ) + h') \quad (6)$$

In Equation (6) above, K, θ1, y, φ, and h' are known values, I can be calculated from Equation (6) above. By substituting the calculated I in Equation (1) above, it is possible to calculate the height h of the convex portion 252.

The convex-lesion-size calculating section 244 determines, according to whether the size h of the convex lesion part is a size within a specified range, whether the convex lesion part is a convex lesion part that should be detected. The convex-lesion-size calculating section 244 outputs a determination result concerning whether the convex lesion part is the convex lesion part that should be detected. For example, the determination result is supplied to the display section 51 via the image processing section 241. Display indicating whether a convex portion being observed is a convex lesion part, display indicating that the convex portion is the convex lesion part, and the like are performed.

In this way, in the present embodiment, by radiating the illumination light on the convex portion from one direction, it is possible to accurately calculate the size of the convex portion. It is possible to surely stanch the convex lesion part that should be detected.

Note that the respective sections in the processor devices 40, 140, and 240 in the respective embodiments may be configured by at least one processor to realize the respective functions according to a program. The respective sections may be respectively configured by hardware to realize the respective functions.

The present invention is not limited to the respective embodiments per se. The constituent elements can be modified and embodies without departing from the spirit of the present invention in an implementation stage. Various inventions can be formed by appropriate combinations of the plurality of constituent elements disclosed in the respective embodiments. For example, several constituent elements of all the constituent elements described in the embodiments may be deleted. Further, the constituent elements described in the different embodiments may be combined as appropriate.

According to the present invention, there is an effect that it is possible to highly accurately detect a size of a convex portion from a picked-up image and specify a lesion part.

What is claimed is:

1. An endoscope system comprising:
    an illumination section that radiates illumination light and illuminates a predetermined illumination range;
    an image pickup sensor that picks up an image of a predetermined image pickup range of a subject illuminated by the illumination section, the image pickup sensor being attached to a distal end of an insertion section of an endoscope and including an optical axis in an axial direction of the insertion section;
    a cylindrical cap attached to the distal end of the insertion section to specify an image pickup range of the image pickup sensor;
    a plurality of illumination-light sources that illuminate the subject with lights in bands different from one another from directions different from one another, the illumination section comprising the plurality of illumination-light sources, the plurality of illumination-light sources being provided on a distal end side of an inner circumferential surface of the cap; and
    a processor comprising hardware, the processor being configured to calculate a size of a convex portion on the basis of a picked-up image obtained by the image pickup sensor when the convex portion is illuminated by illumination lights applied from the plurality of illumination-light sources to the convex portion of the subject.

2. The endoscope system according to claim 1, wherein the plurality of illumination-light sources illuminate the subject from a direction substantially orthogonal to an optical axis of the image pickup sensor.

3. The endoscope system according to claim 1, wherein the processor calculates the size of the convex portion based on a size of the image pickup range.

4. The endoscope system according to claim 1, wherein the processor is further configured to detect the convex portion in a predetermined size range based on a shadow generated adjacent to the convex portion by illumination lights from the plurality of illumination-light sources.

* * * * *